US005864011A

United States Patent [19]
Kuhajda et al.

[11] Patent Number: 5,864,011
[45] Date of Patent: Jan. 26, 1999

[54] CANCER RELATED ANTIGEN

[75] Inventors: Francis P. Kuhajda, Lutherville; Gary R. Pasternack, Baltimore, both of Md.

[73] Assignee: The Johns Hopkins University, Baltimore, Md.

[21] Appl. No.: 469,009

[22] Filed: Jun. 5, 1995

Related U.S. Application Data

[60] Division of Ser. No. 188,426, Jan. 24, 1994, Pat. No. 5,459,791, which is a continuation-in-part of Ser. No. 96,908, Jul. 26, 1993, abandoned, which is a continuation-in-part of Ser. No. 917,716, Jul. 24, 1992, abandoned, and a continuation-in-part of Ser. No. 735,522, Jul. 26, 1991, abandoned, which is a continuation-in-part of Ser. No. 622,407, Dec. 4, 1990, abandoned, which is a continuation of Ser. No. 297,722, Jan. 17, 1989, abandoned.

[51] Int. Cl.$^6$ .................................................... C07K 14/00
[52] U.S. Cl. ........................... 530/324; 530/300; 530/350; 530/806; 530/850; 530/851; 435/69.1; 436/63; 436/64; 436/86
[58] Field of Search ..................................... 530/324, 300, 530/350, 806, 850, 851; 436/63, 64, 86; 435/69.1

[56] References Cited

U.S. PATENT DOCUMENTS

| | | | |
|---|---|---|---|
| 3,535,309 | 10/1970 | Hata et al. | 435/76 |
| 3,630,846 | 12/1971 | Hata et al. | 435/76 |
| 3,897,428 | 7/1975 | Omura et al. | 544/176 |
| 3,909,361 | 9/1975 | Hata et al. | 435/84 |
| 4,000,164 | 12/1976 | Parker | 549/479 |
| 4,011,334 | 3/1977 | Parker | 514/445 |
| 4,032,647 | 6/1977 | Parker | 514/445 |
| 4,110,351 | 8/1978 | Parker | 544/152 |
| 4,328,246 | 5/1982 | Gold | 514/543 |
| 4,602,099 | 7/1986 | Parker | 549/479 |
| 4,738,984 | 4/1988 | Parker | 514/473 |
| 4,789,630 | 12/1988 | Block et al. | 435/5 |
| 4,946,774 | 8/1990 | Oh | 435/7.92 |
| 4,968,494 | 11/1990 | Claremon et al. | 424/94.64 |
| 5,143,907 | 9/1992 | Spielvogel | 514/64 |
| 5,185,149 | 2/1993 | Baldwin et al. | 424/94.63 |
| 5,188,830 | 2/1993 | Atkinson et al. | 424/94.63 |
| 5,190,969 | 3/1993 | Blumenstein et al. | 514/422 |

FOREIGN PATENT DOCUMENTS

| | | |
|---|---|---|
| 0 246 734 | 11/1987 | European Pat. Off. . |
| 0 374 886 | 6/1990 | European Pat. Off. . |
| DD 252 616 | 12/1987 | Germany . |
| 59-255115 | 12/1984 | Japan . |
| 60-058917 | 4/1985 | Japan . |
| 1-132542 | 5/1989 | Japan . |
| 2-113850 | 4/1990 | Japan . |
| 2-247125 | 10/1990 | Japan . |
| WO 89/04963 | 6/1989 | WIPO . |

OTHER PUBLICATIONS

Bacchi, et al., "Effects of Some Antitumor Agents on Growth and Glycolytic Enzymes of the Flagellate Crithidia," Journal of Bacteriology. 98:23–28 (1969).

Furnica, et al., "Mecanismes Biochmiques Impliques Dans La Sensibilisation Des Organismes Vivants Par Des Agents Chimiques A L'Action Des Radiations et Des Cytostatiques," Rev. Roum. Bioshim., 8:117–122 (1971).

Vivants Par Des Agents Chimiques A L'Action Des Radiations et Des Cytosatiques, Rev. Roum. Biochim., 8:117–122 (1971).

Omura, et al., "Relationship Between the Structures of Fatty Acid Amide Derivatives and Their Antimicrobial Activities," Antimicrobial Agents and Chemotherapy, 6:207–215 (1974).

Nery et al., "Isolation and Partial Characterization of Macromolecular Urinary Aggregates Containing Carcinoembryonic Antigen–Like Activity," British Jour. of Cancer (1974) 413–424.

Schroering, et al., "Fatty Acid Synthetiase In Chemically Induced Mammary Carninomas", Res. Communications In Chem. Path. and Pharmocology, (1974) 9:775–778.

Lin, et al., "Fatty Acid Synthetase from a Mouse Mammary Adenocarcinoma", Cancer Research, (1975) 35:3094–3099.

Abraham, et al., "Lipid and Lipogenesis in a Murine Mammary Neoplastic System", in Control Mechanisms in Cancer, Criss, et al eds., pp. 363–378, Raven Press, NY (1976).

Omura, Satoshi, "The Antibiotic Cerulenin, a Novel Tool for Biochemistry as an Inhibitor of Fatty Acid Synthesis," Bacteriological Reviews, 40:681–697 (1976).

Pitot, et al., "Contribution of the Morris Hepatomas to the Biochemistry of Cancer–Establishment of the Phenotypic Heterogeneity of Neoplasms In Vivo", Progress In Cancer Res. and Therapy, (1976) 1:21–37.

Partida, et al., "Comparative Effects of Diphenylglioxal and its Superoxide on Experimental Tumors," Arch. de Farmacol. y Toxicol., 111:231–240 (1977).

Javid et al., "Human Haptoglobins," Curr. Topics in Hematology, (1978), 1:151–192.

Cooper et al., "Acute Phase Reactant Proteins in Cancer," Advances in Cancer Research, (1979), 30:1–44.

Ahmad, et al., "Increase in Fatty Acid Synthetase Content of 3T3–L Cells Undergoing Spontaneuos and Chemically Induced Differentiation to Adipocytes", Biochem. J. (1979) 182:509–514.

O'Brien et al., "Qualitative Analysis of Proteinuria Associated with Bladder Cancer," Investigative Urology, (1979), 17:28–32.

(List continued on next page.)

*Primary Examiner*—Cecilia J. Tsang
*Assistant Examiner*—Bennett Celsa
*Attorney, Agent, or Firm*—Baker & Botts LLP

[57] ABSTRACT

A method of determining the prognosis of a solid tumor is provided, in which a sample from a patient bearing a tumor is assayed for the presence of a protein which is immunologically cross-reactive with the hpr gene product, but not with haptoglobin 1 or haptoglobin 2. Also provided is a method for preparing antibodies specific for this diagnostic marker which correlates with early relapse and metastasis of breast and other cancers. The marker can be detected using immunological methods employing antibodies specific for Hpr protein and not cross-reactive with haptoglobins 1 or 2.

5 Claims, 27 Drawing Sheets

OTHER PUBLICATIONS

Folkersen et al., "Affinity Chromatographic Purification of a New High Molecular Weight Pregnancy Specific Protein–SP–4," Carcino–Embryonic Proteins (1979), 2:503–508.

Davis et al., "Reactions wiht Simple Haptens," Microbiology, 3rd Ed., Harper & Row, pp. 298–306 (1980).

Sutcliffe et al., "Studies on Human Pregnancy–Associated Plasma Protein A," Biochem. Jour. (1980), 191:799–809.

Smith, et al., "Thioesterase II, a New Marker Enzyme for Human Cells of Breast Epithelial Origin," JNCI, 73:323–328 (1981).

Thompson, et al., "Purification and Properties Of Fatty Acid Synthetase From A Human Breast Cell LIne", Biochim. Biophys. Acta, 662:125–130 (1981).

Omura, Satoshi, Chapter 39 "Cerulenin" in Methods in Enzymology, 72:520–532, 1981.

Ahmad, et al., "Inactivation of Rat Mammary Gland Fatty Acid Synthetase By S–(4–bromo–2,3–dioxobutyl)–Coenzyme", Fed. Proc. (1981) 40:1794 Abstract 1463.

Thompson, et al., "Lack of Coordinated Regulation Of Lipogenic Enzymes In A Human Breast Cell Line SKBr3", Biochim. Biophys. Acta, 712:217–220 (1982).

Clements, et al., "Irreversible Inhibition of Fatty Acid Synthase from Rat Mammary Gland with S–(4–bromo–2,3–dioxobutyl)–CoA", Biochem. J. (1982) 207:291–296.

Ahmad, et al., "Studies on Acetyl–CoA Carboxylase and Fatty Acid Synthase from Rat Mammary Gland and Mammary Tumors", Biochem. J. (1982) 208:443–452.

Baseler et al., "Purification of Haptoglobin and Its Effects on Lymphocyte and Alveolar Macrophage Responses," Inflammation, (1983), 7:387–400.

Haram et al., "Serum Protein Pattern in Normal Pregnancy with Special Reference to Acute–Phase Reactants," British Jour. of Obstetrics and Gynaecology (1983), 90:139–145.

Kuhajada et al., "The Distribution of Carcinoembryonic Antigen in Breast Carcinoma," Cancer (1983), 52:1257–1264.

Mendoza, et al., "Thermal Regulation of Membrane Fluidity in *Escherichia coli,*" J. Biol. Chem., 258:2098–2101 (1983).

Spiegelman, et al., "Fibronectin Modulation of Cell Shape and Lipogenic Gene Expression in 3T2–Adipocytes", Cell (1983) 35:657–666.

Bischof, "Placental Proteins," Contributions to Gynecology and Obstetrics (1984), 12:1–5 and 41–74.

Maeda et al., "Duplication Within the Haptoglobin $Hp^2$ Gene," Nature, (1984),309:131–135.

Schindler et al., "Histochemical Localization of Pregnancy –Associated Plasma a in Fetal, Infant. and Adult Organs and Comparison Between Antisers," Gynecol. Obstet. Invest. (1984), 18:88–94.

Bischof, "Placenta Proteins," Contributions to Gynecology and Obstetrics (1984), 12:46–55.

Kuhajda et al., "Pregnancy–Specific Beta–1 Glycoprotein (SP–1) in Breast Carcinoma," Cancer (1984), 54:1392–1396.

Maeda, "Nucleotide Sequence of th Haptoglobin and Haptoglobin–Related Gene Pair," Jour. of Biol. Chem., (1985), 260:6698–6709.

Bensi et al., "Structure ad Expression of the Human Haptoglobin Locus," The EMBO Journal, (1985) 4:119–126.

Kuhajda et al., "Pregnancy–Associated Plasma Protein A:A Clinically Significant Predictor of Early Recurrence in Stage I Breast Carcinom is Independent of Estrogen Receptor Status", Am. J. Pathol. (1985), 121:342–348.

Kuhajda et al., "Pregnancy–Associated Plasma Protein A:A Clinicllly Significant Predictor of Early Recurrence in State II Breast Carcinoma," Hum. Pathol. (1985), 16:228–235.

Ceriani, et al., "Imunohistochemical Studies In Breast Cancer Using Monoclonal Antibodies Against Breast Epithelial Cell Components and With lectins", Devel. Oncol., (1985) 34:233–63.

Hait, et al., "Inhibition of Growth of Leukemic Cells by Inhibitors Of Calmodulin: Phenolthiazines and Metittin," Cancer Chemother. Pharmacol., 14:202–205 (1985).

Pawlak, et al., "Evaluation of Thioesterase II as a Serum Marker for Rat Mammary Cancer," Cancer Research, 46:4712–4719 (1986).

Mowles et al., "A Two–Site Immunoradiometric Assay for Human Pregnancy–Associated Plasma Protein A (PAPP–A) Using Monoclonal Antibodies", Journal of Immunological Methods, (1986) 95:129–133.

Maeda et l., "Polymorphisms in the Human Haptoglobin Gene Cluster: Chromosomes with Multiple Haptoglobin–Related (Hpr) Genes," Proc. Natl. Acad. Sci. USA (1986), 83:7395 7399.

Chemnitz et al., "Comparison of Difference Antibody Preparations Against Pregnancy–Associated Plasma Protein–A (PAPP–A) for Use in Localization and Immunoassay Studies," Br. Jour. of Obstetrics and Gynaecology (1986), 93:916–923.

Fujii, et al., "Effect of Cerulenin, an Inhibitor of Fatty Acid Synthesis, on the Immune Cytolysis of Tumor Cells", Jap. Jap. J. Exp. Med., 56:99–106 (1986).

Chalbos, et al., "Cloning of cDNA Sequences of a Progestin–Regulated mRNA from MCF7 Human Breast Cancer Cells", Nucl. Acids Res., 14:965–981 (1986).

Abraham, et al., "Lipid Metabolism and Enzyme Activities in Hormone–Dependent and Hormone–Independent Mammary Adenocarcinoma in GR Mice", JNCI (1986) 77:233–239.

Weiss, et al., "Fatty–Acid Biosynthesis in Man, a Pathway of Minor Importance", Biol. Chem. Hoppe–Seyler, (1986) 367:905–912.

Oh et al., "An Analogy Between Fetal Haptoglobin and a Potent Immunosuppressant in Cancer," Cancer Res., (1987), 47:5120–5126.

Thompson et al., "Elevated Levels of Abnormally–Fucosylated Haptoglobins in Cancer Sera," British Journ. of Cancer, (1987), 56:5120–5126.

Kuhajada et al., "Molecular Characterization of a human Breast Cancer Antigen Predicting Early Relapse," Lab. Invest. (1987) vol. 56, Abstract 236.

Chalbos, et al., "Fatty Acid Synthetase and Its mRNA Are Induced by Progestins in Breast Cancer Cells", (1987) J. Biol. Chem., 262:9923–9926.

DAKO Corporation, Technical Information and Product List regarding anti–PAPP–A antiserum (1988).

McAllister, et al., "The Effect of Tomour Growth on Liver Pantothenate, CoA, and Fatty Acid Synthetase Activity in the Mouse", Br. J. Cancer (1988) 57:83–86.

Tisdale, et al., "Changes in Host Liver Fatty Acid Synthase in Tumor–Bearing Mice", Cancer Letters (1988) 42:231–235.

Wilder, et al., "Altered Rate and Fatty Acid Distribution in Adriamycin (P388A) Cells", Proceedings of AACR, (1988) 29:318 Abstr. 1265.

Joyeux, et al., "Progestin Increases Gene Transcription and Messenger Ribonucleic Acid Stability of Fatty Acid Synthetase in Breast Cancer Cells," Molecular Endocrinology, 4:681–686 (1989).

Bueler et al., "Antiserum to Pregnancy–Associated Plasma Protein A (PAPP–A) Recognizes Human Haptoglobin", Br. J. Ob. Gyn., (1989), 96:867–869.

Pasternack, et al., "Expression of Haptoglobin–related Protein (Hpr) Epitopes In Human Breast Carcinoma Correlates With Increased Phenotypic Malignancy", J. Cell. Biochem., 138:137, Abstr. E410 (1989).

Shurbaji, et al., "Immhnohistochemical Expression of Hpr In Primary And Metastatic Breast Carcinoma", Lab. Invest., 60:1, Abstr. 525 (1989).

Spydevold, et al., "Activities of Enzymes of Lipid Metabolism in Morris Hepatoma", Biochimica et Biophysica Acta (1989) 1003:80–83.

Funabashi, et al., "Binding Site of Cerulenin in Fatty Acid Synthetase," (1989) J. Biochem., 105:751–755.

Oh, et al., "Monoclonal Antibody to SER Immune Suppressor Detects Polymeric Forms of Haptoglobin," (1989) Hybridoma, 8:449–466.

Romanens, et al., "Cac'ing Safer with Cac'ing Spawning," Der Champignon, 1989, pp. 22–30.

Chambon, et al., "Progestins and Androgens Stimulate Lipid Accumulation In T47D Breast Cancer Cells Via Their Own Receptors", J. Steriod Biochem., 33:915–922 (1989).

Kuhajda et al., "Expression of Haptoglobin–Relaated Protein and its Potential Role as a Tumor Antigen", Proc. Natl. Acad. Sci. USA (1989), 86:1188–1192.

Kuhajda et al., "Haptoglobin–Related Protein (Hpr) Eptiopes in Breast Cancer as a Predictor of Recurence of the Disease", N. Eng. J. Med. (1989) 321:636–641.

Hourdou, et al., "Specific Inhibition of Itrurin Biosynthesis by Cerulenin," Can. J. Microbiol., 36:164–168 (1990).

Amy, et al "Molecular Cloning of the Mammalian Fatty Acid Synthase Gene and Identification of the Promoter Region," Biochem. J., 271:675–679 (1990).

Chalbos, et al., "Expression of the Progestin–Induced Fatty Acid Synthetase in Benign Mastophaties and Breast Cancer as Measured by RNA in Situ Hybridiazation", JNCI, 82:602–606 (1990).

Escot, et al., "Regulation of Fatty Acid Synthetase Ribonucleic Acid In The Human Endometrium During the Menstrual Cycle", J. Clin. Endocrinol. Metab. 70:1319–1324 (1990).

Joyeux, et al., "Effects of Progestins and Menstrual Cycle on Fatty Acid Synthetase nd progestrone Receptor in Human Mammary Glands", J. Clin. Endocrinol. Metab., 70:1438–1444 (1990).

Chalbos, et al., "Progestin–Induced Fatty Acid Synthetase in Breast Cancer", Ann. N. Y. Acad. Sci., 1990, vol. 595, pp. 67–73.

Fawcett, et al., "Identification of the Products of the Haptoglobin–Related Gene," Biochim Biophys. Acta, (1990) 1048:187–193.

Shurbaji, et al., "Expression of Haptoglobin Related Protein (Hpr) Epitopes By Prostate Crcinoma: A Potentiaal Prognostic Indicator", Intl. Acad. Pathol. Mtg., Mar. 1991, Abstr. 300.

Ziegler, et al., "Current Status of Adjuvant Therapy of Early Breast Cancer", Am. J. Clin. Oncol., 14:101–110 (1991) (Abstract only).

Corrigan, et al., "Prognostic Value of the Immunohistochemical Demonstration of Haptoglobin–Related Protein in Breast Cancer", A.J.C.P., Sep. 1991, p. 406, Abstr. 19.

Shurbaji, et al., "Expression of Oncogenic Antigen 519 (OA–519) in Prostate Cancer IS A Potential Prognostic Indicator", Am. J. Clin. Pathol., 97:686–691 (1992).

"Cancer Test Nearing Market", The Daily Record, Oct. 3, 1991, pp. 3, 5.

"In Vitro Cancer Diagnostics", BioWorld Today, Oct. 7, 1991, p. 3.

"New Cancer Analytes: Finally, the Silver Bulltet?", The Genesis Report, Dec. 1991/Jan. 1992, pp. 10–12.

Chalbos, et al., "The Anti–progestin RU486 Stabilizes the Progestin–induced Fatty Acid Cynthetase mRNA but Does Not Stimulates Its Transcription", J. Biol. Chem., 266:8220–8224 (1991).

Reston, et al., "Expression of OA519 (Haptoglobin–Related Protein Epitopes) In Colorectal Carcinomas: Comparison With Molecular Genetic Alterations and Metastis", Lab. Invest., 66:13A (1992), Abstr. 66.

Cote, et al., "Prognostic Features in Breast Carcinoma: Detection of Occult Axillary Lymph Node Micrometastses (LNM), Expression of Hatoglobin Related Binding Protein (OA519) And Progesterone Receptor (PR) in Primary Tumors", Lab. Invest., 66:47A (1992), 77 Abstr. 272.

Redston, et al., "Expression of OA519 (Haptoglobin–Relted Protein Epitopes) In Colorectal and Carcinomas: Comparison With Molecular Gene Alterations and Metastasis", Lab. Invest., 66:47A (1992), Abst. 272.

Martin, et al., "Immunohistochemical Expression of OA–519 In Pre–Neoplstic and Neoplastic Lesion Polyps of the Colon," American Society for Clinical Oncology, (Abstract).

FIG. 3

| Source of Sequence | | |
|---|---|---|
| Experimental | | ILGGHLDAKGSFPWQAKMVS |
| HpR | 93 | KPKNPANPVQRILGGHLDAKGSFPWQAKMVSHHNLTTGATLI |
| Hp-1 | 73 | PKPKNPANPVQILGGHLDAKGSFPWQAKMVSHHNLTTGATLI |
| Hp-2 | 151 | KPKNPANPVQRILGGHLDAKGSFPWQAKMVSHHNLTTGATLI |

FIG. 4A   FIG. 4B  FIG. 4C
 a b c    a b c   a b c
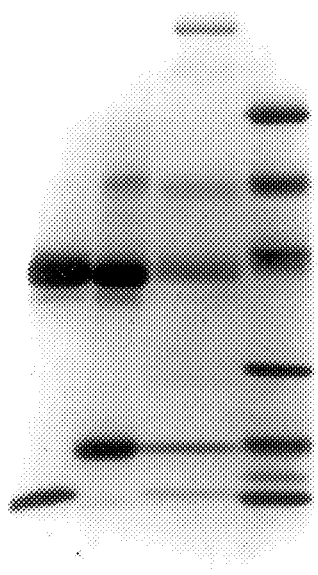
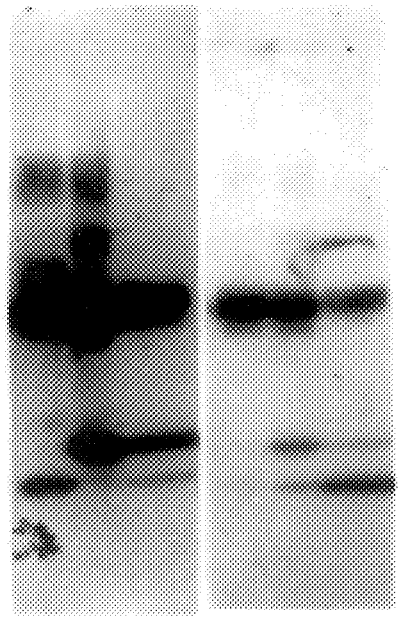

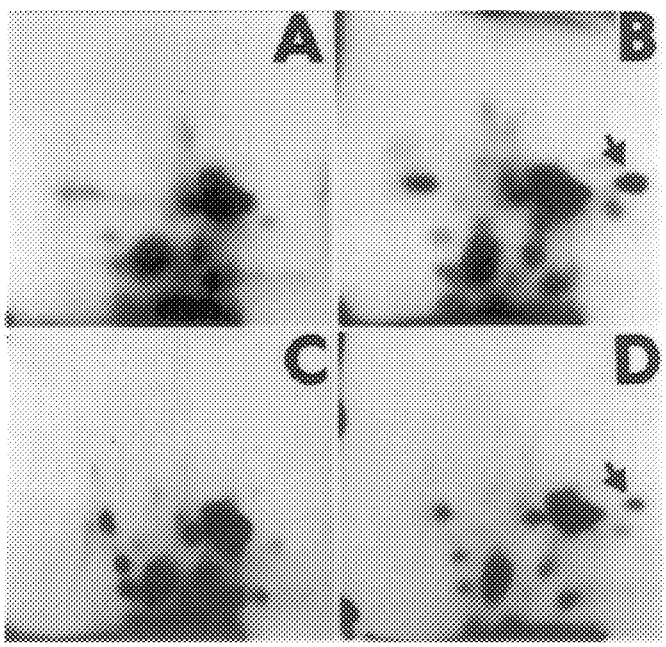

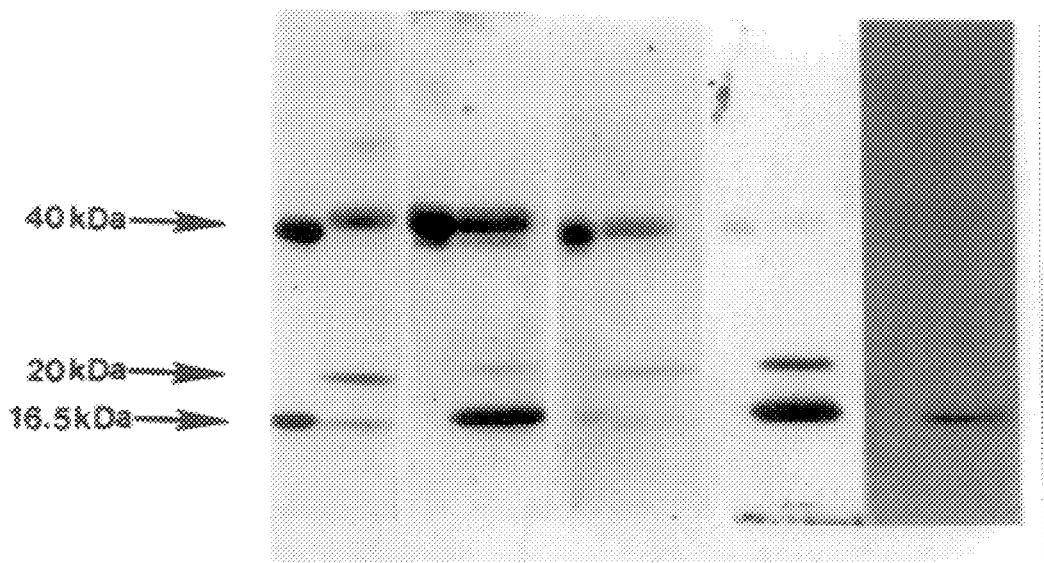

FIG. 12B

Sequence 1: Analysis of 134 kD OA-519 peptide sequence homology.

OA-519 peptide sequence:         LQQHDVAQEQWXP
                                          ||||||| || :|
Rat fatty acid synthase (EC 2.3.1.85):   TKLQQHDVAQGQWDPSGPAPTNLGALD
                                                1290         1300

84.6% identity in 13 amino acid overlap.

Sequence 2: Analysis of OA-519 peptide sequence from Example 12
of the Continuation-In-Part of U.S. Serial No. 07/735522 filed July 26, 1991.

OA-519 peptide sequence:         HAVVLE
                                    ||||||
Rat fatty acid synthase (EC 2.3.1.85):   HAVVLE 100% identity in 6 amino acid overlap.

FIG. 15A
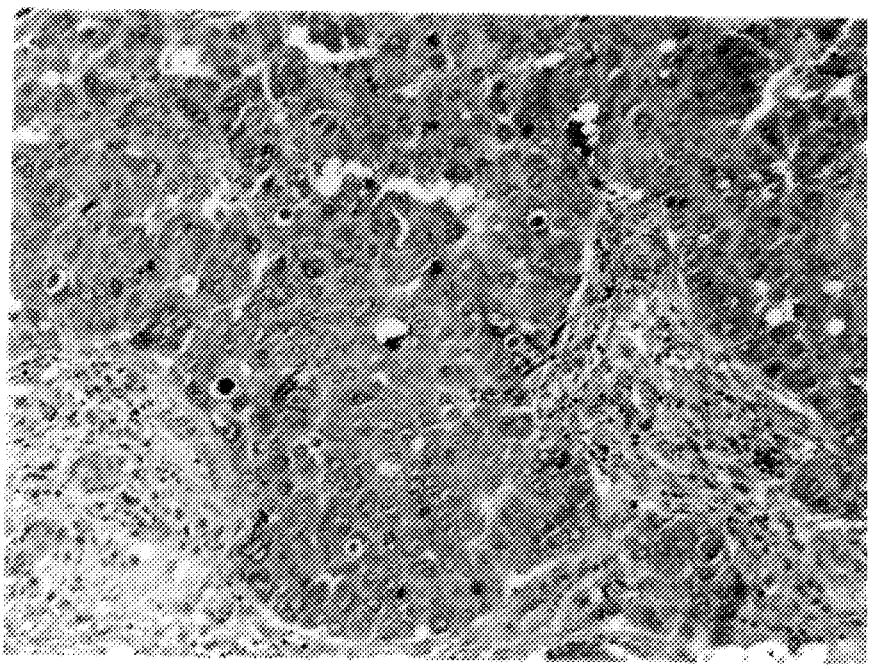
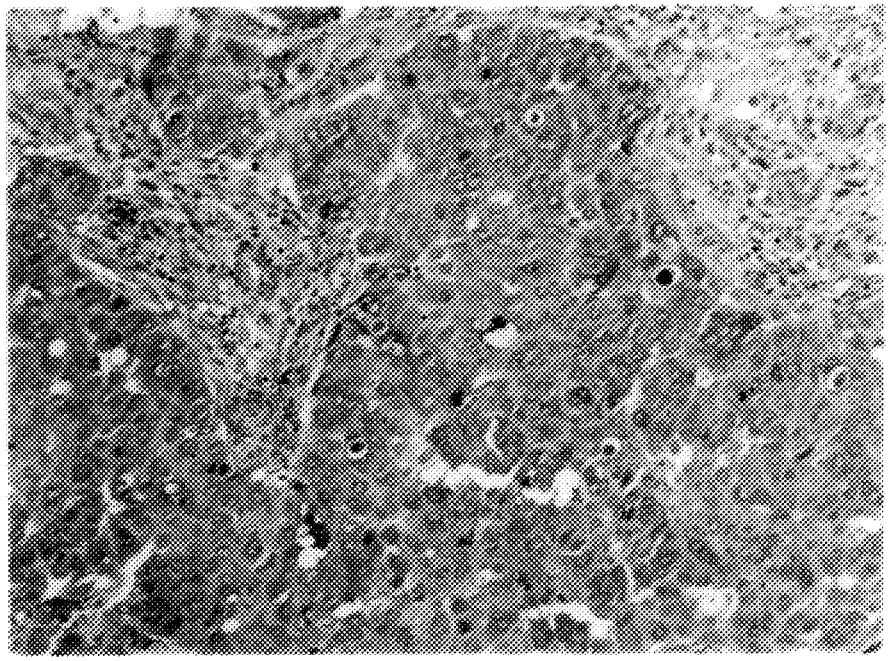
FIG. 15B

FIG. 21
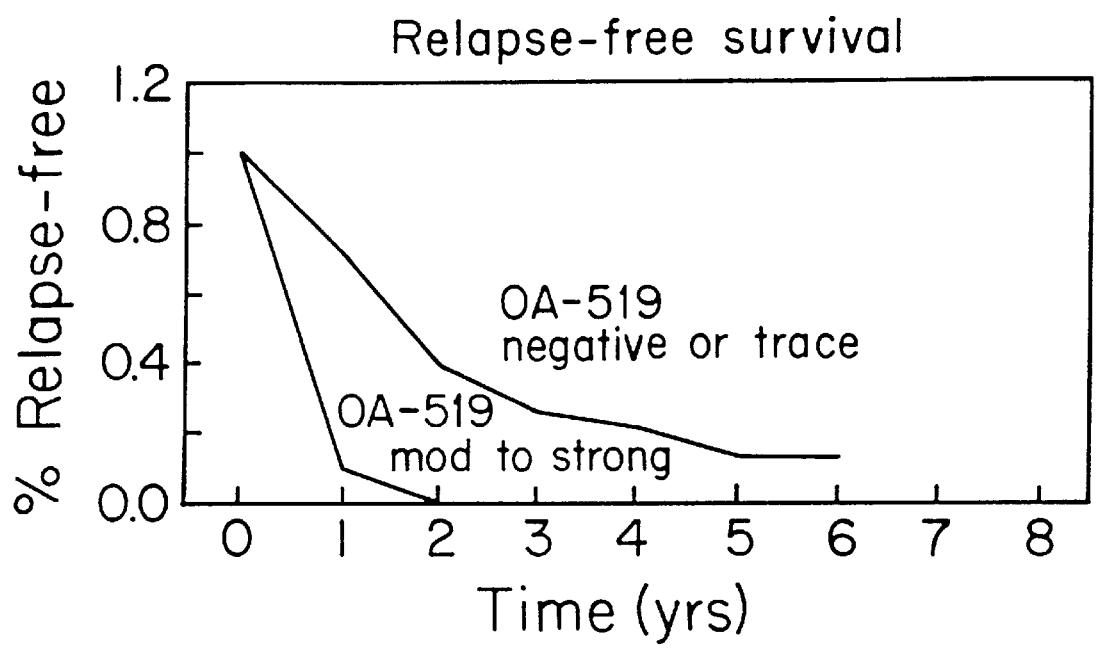
p-value less than .05
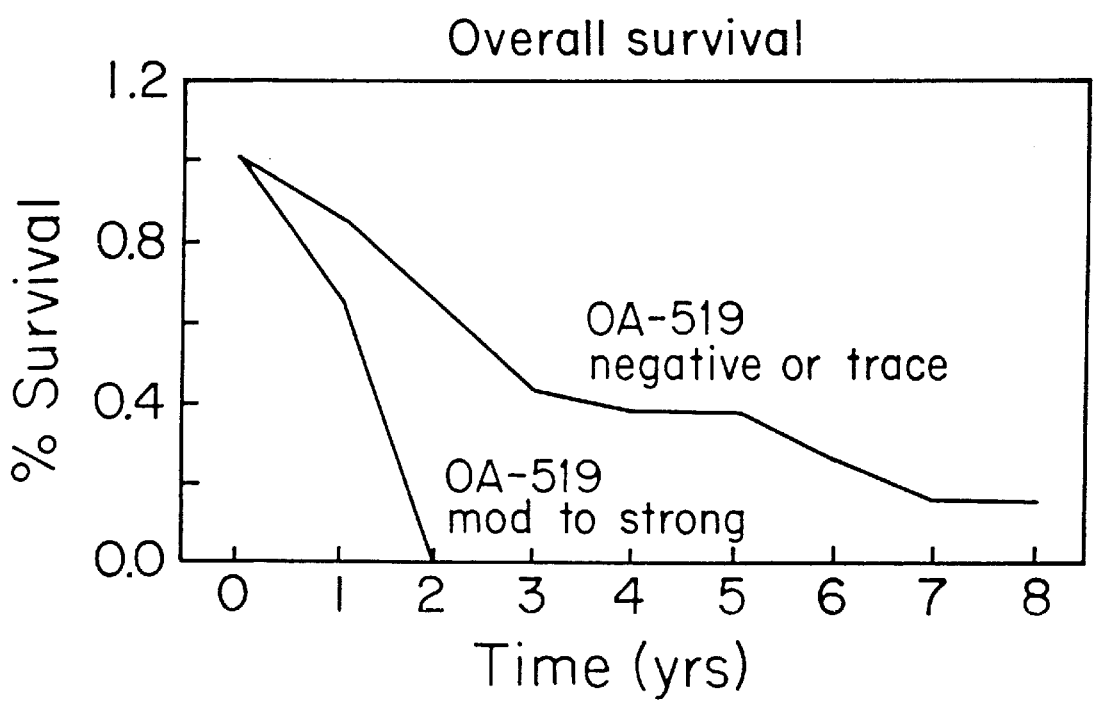
p-value less than .05

NED = No Clinical Evidence of Disease at Time of Measurement ns. Patent No. 5,864,011

CANCER RELATED ANTIGEN

This application is a division of application Ser. No. 08/188,426, filed Jan. 24, 1994 now U.S. Pat. No. 5,759,791 which is a Continuation-In-Part of Ser. No. 08/096,908, filed Jul. 26, 1993 now abandoned, which is a Continuation-In-Part of U.S. Ser. No. 07/917,716, filed Jul. 24, 1992, now abandoned, and a Continuation-In-Part of U.S. Ser. No. 07/735,522, filed Jul. 26, 1991 now abandoned, which is a Continuation-In-Part of U.S. Ser. No. 07/622,407, filed Dec. 4, 1990, now abandoned, which is in turn a Continuation of U.S. Ser. No. 07/297,722, filed Jan. 17, 1989, now abandoned.

The work leading to this invention was supported in part by Grant No. RO1 CA 46143 from the National Institutes of Health. The U.S. Government retains certain rights in this invention.

BACKGROUND OF INVENTION

1. Field of the Invention

This invention relates to the field of human proteins which are expressed by neoplastic tissues and not by most normal tissues.

2. Summary of Related Art

Some carcinoma cells are slow to grow, resulting in tumors that do not pose severe short term risk to a patient having such cells. For instance, many prostate cancers progress so slowly that they are only detected after the patient dies from another cause. Such carcinomas are safely left untreated. Other carcinomas metastasize and grow rapidly, resulting in death of the patient. Any treatment that can slow down the growth of these latter, more virulent carcinomas is desired.

At the time of diagnosis, at least 25 percent of patients with early breast cancer have clinically undetectable metastases. If patients with this status could be identified at the time of diagnosis, one could apply early, intensive chemotherapy to women with clinically occult systemic breast cancer. Conversely, toxic and expensive treatment may be delayed or withheld from patients with favorable prognosis. Traditional associations between the histopathological features and clinical course of the disorder cannot be used to differentiate between clinically aggressive and clinically indolent disease (Hunter, Cancer, 1980, 46:Suppl. 4:961–76). In contrast, several recent studies have demonstrated a relation between changes in oncogenes and prognosis. For example, in some studies, amplification of the HER-2/neu oncogene in patients with breast cancer correlated with overall survival and the disease-free interval between primary therapy and relapse (Slamon, et al., Science, 1987, 235:177–82; Varley, et al., Oncogene, 1987, 1:423–30; and van de Vijver, et al., N. Engl. J. Med., 1988, 319:1239–45). Similarly, changes in both c-myc and c-myb are often identified in aggressive breast cancers (Yokota, et al., Science, 1986, 231:261–5), as is the loss of c-Ha-ras alleles (Theillet, et al., Cancer Rest, 1986, 46:4776–81). The molecular genetic approach is promising both clinically, as a potential diagnostic and prognostic aid, and scientifically, as a means to explore the biology of neoplasia.

SUMMARY OF THE INVENTION

It is an object of the invention to provide a method of determining the prognosis of a solid tumor-bearing patient.

It is yet an additional object of the invention to provide a kit and method for breast cancer prognostication.

It is yet another object of the invention to provide a method to aid in detecting an increase in the number of tumor cells in a patient.

It is another object of the invention to provide a preparation of antibodies which is immunoreactive with a protein whose presence is correlated with a worsened prognosis in a solid tumor bearing patient but not immunoreactive with haptoglobin 1 or 2.

It is an object of the invention to provide a substantially pure preparation of a polypeptide having an amino acid sequence corresponding to the nucleotide sequence of the hpr gene and having the ability to stimulate the production of antibodies in a mammal which are immunoreactive with epitopes found on the hpr gene product but not found on haptoglobin 1 or 2.

These and other objects of the invention are provided by one or more of the embodiments described below.

A gene encoding a theoretical protein, whose sequence is highly homologous to but distinct from that of haptoglobin, was reported in the literature, and the gene was designated hpr (for haptoglobin related protein). The present inventors first discovered that a protein corresponding to this gene was actually expressed in humans, and further that the protein reacted with antibodies that were not immunoreactive with haptoglobin. These antibodies were designated "anti-Hpr" antibodies. Despite the fact that, unlike haptoglobin, synthesis of the hpr gene product has not been found in the liver, the present invention provides four different sources which do contain material reactive with Hpr-specific antibodies. Human breast carcinoma cells, human decidua, human placenta, and human pregnancy serum have all been found to contain material specifically cross-reactive with Hpr-specific antibodies.

In the parent application, U.S. Ser. No. 07/297,722, the protein found in the cytoplasm of breast carcinoma cells which was reactive with anti-Hpr antibodies was called Hpr protein. However, as shown herein, the protein from tumor cells differs in sequence and physical properties, and so the inventors now refer to this cytoplasmic protein as OA-519. OA-519 has been found to be an especially useful diagnostic marker in human solid tumors for predicting the propensity for tumor invasion and early metastasis. The inventor's new terminology, OA-519, is used generally in this disclosure in place of "Hpr protein" to refer to the cytoplasmic protein from tumor cells which is cross-reactive with the hpr gene product but not with haptoglobin 1 or haptoglobin 2 (Hp1 or Hp2).

In one embodiment a substantially pure preparation of polypeptide is provided having an amino acid sequence corresponding to the nucleotide sequence of the hpr gene. When the preparation of the polypeptide is administered to a mammal, it stimulates the production of antibodies which are immunoreactive with epitopes found on the hpr gene product but which are not found on haptoglobin 1 or 2. In another embodiment of the invention a preparation of such antibodies is provided.

In yet another embodiment of the invention a preparation of Hpr protein is provided which is substantially purified from Hp1 and Hp2.

In still another embodiment of the invention, a method of producing a preparation of a protein cross-reactive with the hpr gene product but not with haptoglobin 1 or 2 is provided. Human breast carcinoma cells are tested for immunoreactivity with antibodies which are reactive with epitopes present on the hpr gene product but not present on Hp1 or 2. Immunoreactive breast cancer cells are cultured and a cytoplasmic fraction containing a protein cross-reactive with the hpr gene product but not with haptoglobin 1 or 2 is harvested from the cultured cells. The cross-reactive protein (OA-519) may be purified by physicochemical or immunoaffinity methods, and antibodies may be produced by immunizing a mammal with the protein. In yet another embodiment, the invention provides a preparation of antibodies which immunologically bind OA-519, the cross-reactive protein from the cytoplasm of breast carcinoma cells.

In still another embodiment of the invention a method is provided for detecting proliferation of tumor cells in a patient. A sample is collected from a patient bearing a tumor. The amount of material cross-reactive with the hpr gene product but not with Hp1 or 2 in the sample is quantitated. The amount of the cross-reactive protein found in the sample is compared to the amount found in a control sample collected from a patient with no detectable tumor. An elevated amount of the cross-reactive protein in the tumor-bearing patient's sample indicates proliferation of the tumor cells.

In another embodiment a kit for determining the prognosis of breast carcinoma is provided. The kit comprises a preparation of antibodies which is immunoreactive with epitopes present on a protein cross-reactive with the hpr gene product but not present on haptoglobin 1 or 2 and a means for detecting the antibodies. A method of prognosticating the course of a solid tumor is also provided wherein histological sections are contacted with a preparation of antibodies which is immunoreactive with a protein cross-reactive with the hpr gene product but not with haptoglobin 1 or 2. Antibody binding to the sections is determined.

In yet another embodiment of the invention a method is provided for assaying a biological fluid for the presence of a protein which is cross-reactive with the hpr gene product but not with haptoglobin 1 or haptoglobin 2. Antibodies immunoreactive with an epitope found on a protein cross-reactive with the hPr gene product but not found on Hp1 and Hp2 are attached to a solid support which is then contacted with a biological fluid containing an unknown quantity of the cross-reactive protein under conditions where antibody-antigen complexes form and are stable. The solid support is then contacted with a polypeptide which shares an epitope with the protein cross-reactive with the hpr gene product but not with Hp1 and Hp2, under conditions where antibody-antigen complexes form and are stable. The polypeptide also bears a detectable moiety so that the amount of polypeptide bound to the solid support can be quantitated by detecting and quantitating the detectable moiety. A control is performed wherein no biological fluid is contacted with the solid support, to determine 100% binding of the polypeptide to the support. The amount of binding reduction observed in the presence of biological fluid is correlated to the amount of the protein cross-reactive with the hpr gene product in the biological fluid.

These and other embodiments are disclosed below in the detailed description of the invention.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 3 depicts sequences of: (1) protein predicted from the hpr gene sequence; (2) haptoglobin 1; and (3) haptoglobin 2, each of which aligns with the N-terminal beta chain sequence of the protein isolated from pregnancy serum.

FIGS. 4A–4C show polyacrylamide gel electrophoretic separation of haptoglobin 1, haptoglobin 2, and purified pregnancy associated protein (hpr gene product). The gel in FIG. 4A is Coomassie stained; the gel in FIG. 4B is a corresponding immunoblot with anti-haptoglobin antisera; and the gel in FIG. 4C is a corresponding immunoblot with anti-PAPP-A antisera.

FIG. 5A–5D show tryptic peptide maps of haptoglobin alpha chains of haptoglobin 1 (FIG. 5A), hpr gene product (FIG. 5B), haptoglobin 2 (FIG. 5C), and a mixture of haptoglobins (FIG. 5D).

FIGS. 6A–E show polyacrylamide gel electrophoresis of haptoglobin 1 and hpr gene product. Panels B–E are immunoblots of the same proteins with various antibody preparations.

FIG. 12B shows the peptide sequence analysis of OA-519.

FIG. 15 shows immunohistochemical staining of human breast carcinoma using antibodies raised against the synthetic peptide.

FIG. 21 shows the correlation between OA-519 expression and prognosis in ovarian carcinoma. The upper panel of FIG. 21 shows relapse free survival and the lower panel of FIG. 21 shows overall survival.

DETAILED DESCRIPTION OF THE INVENTION

Figure 1:
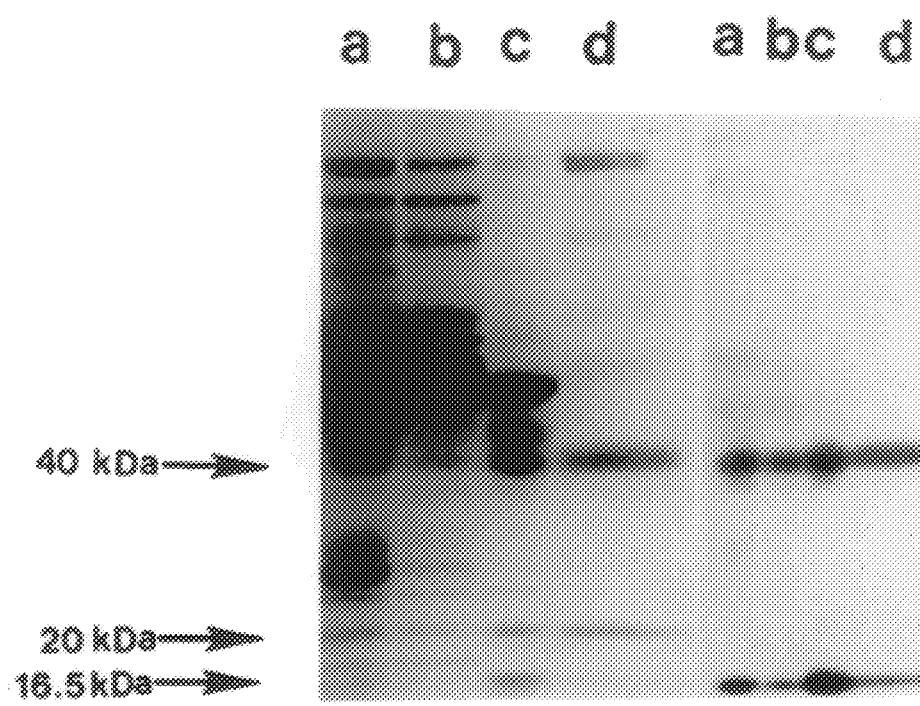
FIG. 1 shows the progressive purification of the hpr gene product. Polyacrylamide gel electrophoresis and corresponding western blots are shown of sequential chromatographic purification of plasma proteins reactive with anti-PAPP-A poly specific antibodies to pregnancy-associated plasma protein A, obtained from DAKO Laboratories.

In 1985, Maeda (*J. Biol. Chem.*, vol. 260, pp. 6698–6709, which is expressly incorporated herein), described a stretch of DNA located 2.2 kb downstream from the conventional haptoglobin locus. The DNA sequence indicated that the locus contained an intact gene coding for a theoretical protein whose alpha and beta chains are distinct from, but highly homologous to, conventional haptoglobins. Maeda called this locus hpr for "haptoglobin related." Several investigators failed to detect expression of this gene. (Oh, et al., Cancer Research, vol. 47, pp. 5120–5126, 1987; Maeda, *Journal of Biological Chemistry*, vol. 260, pp. 6698–6709, 1985; and Bensi et al., The EMBO Journal, vol. 4, pp. 119–126, 1985.)

A synthetic polypeptide has been made having the following amino acid sequence: leu-tyr-ser-gly-asn-asp-val-thr-asp-ile-ser-asp-asp-arg-phe-pro-lys-pro-pro-glu-ile-ala-asn-gly-tyr-val-glu-lys-leu-phe-arg-tyr-gln-cys which is identified as SEQ ID NO. 1. This polypeptide generally corresponds to the 34 N-terminal amino acids predicted from the nucleotide sequence of the hpr gene as identified by Maeda. This peptide is able to stimulate the production of antibodies in a mammal which are immunoreactive with epitopes found on the hpr gene product but which are not found on either haptoglobins 1 or 2. These antibodies can be used to reliably detect expression of the hpr gene in any human tissue as well as to purify the gene product using immunoaffinity techniques, which are well known in the art.

Conventional human haptoglobins have been well studied; they were discovered over 40 years ago and their role is thought to be in the plasma transport of free hemoglobin. Haptoglobin synthesis occurs mainly in the liver, although in some cases lymphocyte cultures and brain have been reported to synthesize haptoglobins. All haptoglobins contain two classes of polypeptide chains, beta chains and alpha chains. Beta chains are almost identical in all haptoglobins, whereas the alpha chains have been found in three forms. Two of the alpha chain forms (Hp1$^f$ and Hp1$^s$) differ only in a single amino acid residue at position 54. The third form (Hp2) is longer than either of the other two alpha chains, apparently having arisen by an unequal crossing over to partially duplicate the alpha chain.

It is a finding of the present invention that proteins, which are cross-reactive with a peptide according to SEQ ID NO. 1 which has hitherto been undetected, can be found in various human cells and tissues. These include: human breast carcinoma tissue, human decidua and placenta, serum from pregnant women, and cultured human breast carcinoma cell lines. The cross-reactive protein from pregnancy serum has been purified using physicochemical methods to be substantially pure of Hp1 and Hp2. The protein from pregnancy serum has an amino acid sequence corresponding to the nucleotide sequence of the hpr gene, and as predicted from its nucleotide sequence, it is very similar to haptoglobins 1 and 2, although there are a number of amino acid differences which cluster at the N-terminus of the alpha chain. This protein is called Hpr protein hereinafter.

The cross-reactive protein from the cytoplasm of cultured human breast carcinoma cell lines has also been purified by physiochemical methods to be substantially pure. cDNA encoding this cross-reactive protein has been cloned and the nucleotide sequence determined. Cloned plasmids pFAS 1.6, pFAS 3.0, pFAS 2.2, and pFAS 4.6 were deposited under ATCC Accession Nos. 75643, 75645, 75644, and 75646, respectively (see clone map in FIG. 12D). The sequence of this cytoplasmic protein is substantially unrelated to the sequence of the hpr gene, and the cytoplasmic protein is called OA-519 hereinafter. The sequence of OA-519 is highly homologous with rat fatty acid synthase.

The substantially pure preparation of polypeptide having an amino acid sequence corresponding to the nucleotide sequence of the hpr gene can be made using any of the techniques which are known in the art. For example, the Merrifield technique (*Journal of the American Chemical Society*, vol. 85, pp. 2149–2154, 1968), can be used. Substantial purity means that the preparation is almost totally free of haptoglobins 1 and 2. Polypeptides may be designed by comparing the amino acid sequences of Hpr protein, haptoglobin 1 and haptoglobin 2, and utilizing those regions of sequence which have the maximum amount of differences. The hpr gene sequence can be obtained from the publication of Maeda, *Journal of Biological Chemistry*, vol. 260, pp. 6698–6709, 1985, and the haptoglobin 1 and 2 sequences can be obtained from the database of the National Biomedical Research Foundation as well as from Kurosky, *Proceedings of the National Academy of Sciences U.S.A.*, vol. 77, pp. 3388–3392, 1980; Black et al., *Nature*, vol. 218, pp. 736–741, 1968; Black et al. *Canadian Journal of Biochemistry*, vol. 48, pp. 123–132, 1970; and Black et al. *Canadian Journal of Biochemistry*, vol. 48, pp. 133–146, 1970.

Although a sequence which corresponds to the 34 N-terminal amino acids of the predicted Hpr protein has been used, other polypeptides can be used as well. Other polypeptides may be made which are longer or shorter or have conservative amino acid changes which do not change the epitope(s) found on proteins cross-reactive with the hpr gene product but not found on Hp1 or Hp2. Preferred polypeptides for immunizing will have the sequence of OA-519, or a fragment of the sequence of OA-519 which is able to stimulate antibody production. Such fragments will usually contain at least 6 amino acids of the OA-519 sequence and frequently more than 10 amino acids of the sequence. The peptide fragments from the OA-519 sequence will usually be hydrophilic and represent a mobile sequence (not conformationally constrained). Preferably, the fragment of OA-519 will contain a sequence which is unique to human fatty acid synthase.

Polypeptides can be tested to determine if they are able to stimulate mammals to produce antibodies which are immunoreactive with epitopes found on proteins cross-reactive with the hpr gene product but not found on Hp1 or Hp2. Methods of immunizing mammals to stimulate antibody production are well known in the art. Methods for testing the immunoreactivity of antibodies for known antigens are also well known.

A substantially pure preparation of a polypeptide of the present invention can be used to affinity purify antibodies specific for the proteins cross-reactive with the hpr gene product. In addition, the preparation of polypeptide of the present invention can be used to stimulate production of antibodies in a mammal by immunizing the mammal with the preparation. Usually, such immunization will employ coupling of the polypeptide to a larger immunogenic substance such as keyhole limpet hemocyanin. For affinity purification purposes, the polypeptide can be coupled to an inert matrix, such as agarose beads. Techniques for such coupling are well known in the art. The preparation of the polypeptide can also be used to quantitate Hpr-specific antibodies in an antibody preparation. In such a case, the synthetic peptide will usually be coupled to a larger inert proteinaceous substance such as bovine serum albumin. Once again, the techniques for coupling polypeptides to such matrices are well known in the art.

Purification of Cross-Reactive Protein

Applicants have found proteins cross-reactive with the hpr gene product in four different human cell types. Three of these cell types can practically be used to produce amounts of proteins cross-reactive with the hpr gene product for biochemical studies as well as studies to determine the biological effect of these proteins under physiological conditions. One particularly useful source is human breast carcinoma cell lines, which can be obtained from the American Type Culture Collection in Rockville, Md. One such cell line is called MDA-MB-231, and is an estrogen receptor negative cell line. Other such cell lines include ZR-75-1 and SK-Br-3. Hpr epitopes have been detected in the cytoplasm of about 50% of such breast carcinoma cell lines. Those cell lines readily can be identified, e.g., by use of antibodies immunoreactive with the polypeptide described above, having the 34 amino acid in SEQ ID NO. 1.

One means of preparing an Hpr-reactive protein preparation is to culture the human breast carcinoma cells which produce such a protein using culture conditions which are well-known in the art. The cells are then harvested and the cell membrane disrupted to obtain a cell lysate. The nuclei and membrane fractions can be removed and a cytoplasmic fraction containing proteins cross-reactive with the hpr gene product is obtained. Means of separating various cellular fractions, such as differential centrifugation, are indeed well-known in the art. Similarly, histological sections of breast tumors contain proteins cross-reactive with the hpr gene product, but this is a difficult tissue source to obtain in a quantity and manner permitting purification of the proteins.

Proteins cross-reactive with the hpr gene product have also been found in human decidua tissue and placenta. Such tissue can be collected from different sources and homogenized according to techniques well-known in the art. The cell membrane of the homogenized cells of the tissue can then be lysed to obtain a cytoplasmic fraction containing proteins cross-reactive with the hpr gene product. Serum from pregnant women has also been shown to contain proteins cross-reactive with the hpr gene product in recoverable amounts.

Once a cytoplasmic fraction containing proteins cross-reactive with the hpr gene product is obtained, purification of the protein of can be accomplished according to techniques which are well-known in the protein purification art. For example, various types of chromatography may be used. Columns which have been found to be particularly useful include a CIBACRON F3GA SEPHAROSE column, a DEAE cellulose column, an anion exchange column, as well as a gel permeation column.

Proteins cross-reactive with the hpr gene product but not with haptoglobin 1 or haptoglobin 2 can also be purified using immunoaffinity techniques. Antibodies are provided herein which are specific for epitopes found on proteins cross-reactive with a peptide according to SEQ ID NO. 1 but not found on haptoglobin 1 or haptoglobin 2, and the cross-reactive proteins can be positively selected from a mixture of many proteins by binding to these antibodies. The use of the antibodies of the present invention to purify the proteins allows good separation from the proteins which are most similar to Hpr protein, namely haptoglobins 1 and 2. Of course, other techniques of purification are known in the art and can be used to purify the proteins of this invention.

The protein preparations which are obtained according to the present invention are substantially pure and probably homogeneous. This conclusion is based on visualization of proteins electrophoretically separated on polyacrylamide gels. In gels of Hpr protein purified from pregnancy plasma, no haptoglobin 2 is detected. Generally, substantially pure preparations are free of Hp1 and Hp2 and will have greater than 75% of the haptoglobin-type protein present being Hpr protein. More preferably, the preparations will contain greater than 90% of the haptoglobin type protein as Hpr protein. Gels of OA-519 purified from the cytoplasm of tumor cells or cell lines also show substantially pure protein.

Recombinant Production of Cross-Reactive Protein

It is possible to purify a cross-reactive protein from an appropriate tissue/fluid source; however, a cross-reactive protein or polypeptide may also be produced by recombinant methods from a DNA sequence encoding such a protein or polypeptide, which DNA sequence can be synthesized chemically or isolated by one of several approaches. The complete sequence may be assembled from overlapping oligonucleotides prepared by standard methods and assembled into a complete coding sequence. See, e.g., Edge (1981) *Nature* 292:756; Nambair, et al. (1984) *Science* 223:1299; Jay, et al. (1984) *J. Biol. Chem.*, 259:6311. The isolation methods will rely in part on nucleic acid hybridization using appropriate single stranded or double stranded nucleotide or oligonucleotide probes. Such probes can be constructed synthetically, based on the DNA or amino acid sequences disclosed herein, or isolated from genomic or cDNA clones also described herein.

The basic strategies for preparing oligonucleotide probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). First, a DNA library is prepared. The library can consist of a genomic DNA library from a human source. Human genomic libraries are known in the art. More preferred are DNA libraries constructed of cDNA, prepared from poly-A-plus RNA (mRNA) by reverse transcription. The mRNA is isolated from a cell line or tissue believed to express the protein cross-reactive with a peptide according to SEQ ID NO.1, such as a human breast carcinoma cell line. A suitable source of MRNA for cDNA library constructions is the cell line ZR-75-1. The genomic DNA or cDNA is cloned into a vector suitable for construction of a library. The construction of an appropriate library is within the skill of the art. See, e.g., B. Perbal, supra. Once the library is constructed, oligonucleotides are used to probe the library to identify the segment carrying a sequence encoding a cross-reactive protein, such as OA-519.

Nucleic Acid Probes

Oligonucleotides can be designed and produced for use as hybridization probes to locate the other coding sequences. In general, the probes are synthesized chemically, preferably based upon known nucleic acid sequences, such as the sequences of the clones shown in FIG. 12D. Ultimately, the isolated segments of DNA are ligated together in such a way that the correct mature protein is encoded.

However, it may become necessary to obtain internal sequences from the protein. This can be done, for example, by Staph-V8 proteolysis of protein purified in the usual way, which may be followed by reductive alkylation and separation by HPLC of the digestion products. Elution peaks corresponding to discrete enzyme fragments can then be sequenced by standard methods. Nucleotide sequences encoding portions of the protein can be predicted from the amino acid sequence. Nucleotide sequences are selected so as to correspond to codons encoding the amino acid sequence. Since the genetic code is redundant, it will usually be necessary to synthesize several oligonucleotides to cover all, or a reasonable number, of the possible nucleotide sequences which encode a particular amino acid sequence. Thus, it is generally preferred, in selecting a region of the sequence upon which to base the probes, that the region not contain amino acids whose codons are highly degenerate. It may not be necessary, however, to prepare probes containing codons whose usage is rare in humans (from which the library was prepared). Alternative methods using a long probe (greater than 35 bp) which is not degenerate may also be used as described by Lathe, R. (1985), J. Mol. Biol., 183:1–12 (discussed in Sambrook, et al.).

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 1000 nucleotides in length, more typically they are not greater than 500 nucleotides, even more typically they are no greater than 250 nucleotides; they may be no greater than 100 nucleotides, and also may be no greater than 75 nucleotides in length. Generally it is recognized in the art that probes from about 14 to about 20 base pairs are usually effective. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

Selection of Clones

As is known in the art, oligonucleotide probes are usually labeled with a marker, such as a radionucleotide or biotin, using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors including, but not limited to, the length of the probe, whether the probe and library are from the same species, and whether the species are evolutionarily close or distant. It is within the skill of the art to optimize hybridization conditions so that homologous sequences are isolated and detectable above background hybridizations. The basic requirement is that hybridization conditions be of sufficient stringency so that selective hybridization occurs; i.e., hybridization is due to a minimum degree of nucleic acid homology (e.g., at least about 75%), as opposed to non-specific binding or hybridization due to a lower degree of homology. See generally, "Nucleic Acid Hybridization," (1985) B. D. Hames and S. J. Higgins, eds.

Where the library is an expression library, selection may be accomplished by expressing the library sequences and detecting the expressed peptides immunologically. Clones which express peptides which bind the antibodies of this invention are selected. These selection procedures are well known to those of ordinary skill in the art (see, e.g., Sambrook, et al.).

Alternatively, a nucleic acid whose sequence corresponds to the sequence of OA-519 may be used to detect chromosomal alterations such as amplifications, translocations, deletions and mutations using fluorescent in situ hybridization, Southern blot analysis, dot blot analysis, the polymerase chain reaction, or semi-quantitative modifications of the polymerase chain reaction. A nucleic acid whose sequence corresponds to the sequence of OA-519 may be used to select genomic clones corresponding to the OA-519 gene. Nucleic acids corresponding to the OA-519 gene may be characterized by standard sequencing techniques and may also be used in any of the foregoing assays.

Cloning for Expression

Once a coding sequence for the desired polypeptide sequence has been prepared or isolated, it can be cloned into any suitable vector or replicon and thereby maintained in a composition which is substantially free of vectors that do not contain the coding sequence (e.g., free of other clones from the library). Numerous cloning vectors are known to those of skill in the art, and the selection of an appropriate cloning vector is a matter of choice (see, e.g., Sambrook, et al., incorporated herein by reference). The DNA sequences and DNA molecules of the present invention may be expressed using a wide variety of host/vector combinations. According to the present invention, the coding sequence for the polypeptide which is cross-reactive with the hpr gene product is placed under the control of a promoter, ribosome binding site (for bacterial expression) and, optionally, an operator (collectively referred to herein as "control" elements), so that the DNA sequence is transcribed into RNA in the host cell transformed by a vector containing this expression construct. The coding sequence may or may not contain a signal peptide or leader sequence.

Of course, not all host/expression vector combinations function with equal efficiency in expressing the DNA sequences of this invention or in producing the polypeptides of this invention. However, a particular selection of a host/expression vector combination may be made by those skilled in the art. For example, the selection should be based on a balancing of a number of factors. These include compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein. Preferably, the host cell will not express proteases which degrade the recombinant polypeptide of this invention.

Depending on the expression system and host selected, the protein is produced by growing host cells transformed by an expression vector containing the coding sequence for a polypeptide cross-reactive with the hpr gene product under conditions whereby the protein is expressed. The protein is then isolated from the host cells and purified. The selection of the appropriate growth conditions and recovery methods are within the skill of the art.

Production of Antibodies

Mammals immunized with the hpr gene product, with a peptide whose sequence is listed as SEQ ID NO. 1, or with a protein cross-reactive with a peptide whose sequence corresponds to SEQ ID NO. 1, will produce polyclonal antibodies contemplated by this invention. As mentioned above, antibodies which are specific for the Hpr protein in that they are immunoreactive with Hpr protein but not with either haptoglobins 1 or 2 can be made using a synthetic polypeptide of the present invention. Preferred polypeptides for use in immunizing mammals to obtain antibodies according to this invention will have all or part of the amino acid sequence of OA-519. Immunization of mammals such as rabbits, mice, goats, etc. to produce antibodies is well known in the art. Polyclonal antibody preparations can be partially purified using immunoaffinity techniques employing a synthetic polypeptide of the present invention. Immunoaffinity purification of polyclonal antibodies may also employ proteins purified according to this invention, or polypeptide fragments of such proteins. Such purification methods are well-known in the art.

Monoclonal antibodies can also be raised which are specific for Hpr epitopes and do not cross-react with haptoglobin 1 or 2. Generally, a rat or mouse will be immunized with the synthetic polypeptide of the present invention (or a protein cross-reactive with a peptide according to SEQ ID NO. 1) and the rodent will later be sacrificed and spleen cells recovered for fusion with myeloma cells. Hybrid cells can be selected according to techniques known in the art, for example, selections involving complementation of two phenotypes, one from each parental cell. Antibody production of each hybrid cell can be screened individually. Antibodies which bind to epitopes on proteins cross-reactive with Hpr protein but not on Hp1 or Hp2 may bind Hpr or any other protein expressing these epitopes. In one embodiment of this invention, monoclonal antibodies are selected which bind to OA-519, but do not bind to Hpr.

In order to screen for antibodies which are immunoreactive with epitopes found on proteins cross-reactive with the hr gene product but not found on Hp1 or Hp2, a simple battery of tests can be performed. (1) Antibodies can be tested for immunoreactivity with proteins cross-reactive with Hpr protein using a substantially pure preparation of Hpr protein or a cross-reactive protein, or with the preparation of polypeptide of the present invention conjugated to a larger moiety such as bovine serum albumin. The desired specific antibodies should be positive in either or both of these tests. (2) The antibodies should also be tested for immunoreactivity with Hp1 and Hp2. Desired antibodies having absolute specificity for Hpr protein or a cross-reactive protein should be negative in both such tests.

Antibodies can also be detected using this battery of tests which have relative specificity for Hpr protein relative to Hp1 and Hp2. That is, some monoclonal antibodies can be found which react more strongly with Hpr protein than with Hp1 and Hp2. These antibodies of relative specificity for Hpr protein may also be useful. Means for using them are discussed below.

Antibodies that are immuno-reactive with OA-519 but not Hpr can be selected using similar tests. In particular, these antibodies are positive in tests for binding to purified OA-519 and negative in tests for binding to purified Hpr. These antibodies are preferred for use in assays of serum or blood for the presence of OA-519.

Immunoaffinity techniques can be used to purify monospecific polyclonal antibodies specifically reactive with a protein cross-reactive with a peptide according to SEQ ID NO. 1 but not with Hp1 or Hp2. Similar binding properties are employed as in the tests described for monoclonal antibodies above. That is to say that antibodies which immunoreact with Hpr protein or a cross-reactive protein will be positively selected, while those that immunoreact with Hp1 and Hp2 will be removed from the desired antibody preparation.

Antibodies which show relative or preferential specificity for Hpr protein relative to Hp1 and Hp2 can be rendered absolutely specific by altering the conditions under which immunoreactivity is assayed. Conditions in the assay medium which can be altered include, but are not limited to: the ionic strength; the detergent concentration; the concentration of chaotropic agents, such as urea, guanidine, and potassium thiocyanate; and the pH. Alteration of these conditions leads to destabilization of the various bonding forces which contribute to antibody-antigen binding. Titration of reagents altering each of these conditions allows determination of a set of conditions where relatively or preferentially specific antibodies immunoreact with Hpr protein but not with Hp1 or Hp2. Suitable ranges in which to vary the destabilizing agent concentrations can readily be determined. For example, in order to alter ionic strength, potassium chloride can be titrated from about 0.05M to 2M. Detergents, either ionic or non-ionic, can be titrated from about 0.05% to 2%. Chaotropic agents can be titrated from about 0.5M to 8M. The range of pH can be titrated from about 2 to 10. Such conditions can be useful both to screen for monoclonal antibodies immunoreactive with Hpr epitopes and to assay for proteins containing such epitopes in various biological sources. The above-described method of titrating various destabilizing agents can also be used with other antibody-antigen pairs to enhance the specificity of reaction.

Diagnostic Assays

Detection of proteins cross-reactive with the hpr gene product but not with haptoglobin 1 or 2, and their expression, may be on the nucleotide or peptide level. Antibodies can be prepared by immunizing mammals with peptides expressed from nucleic acid sequences corresponding to cross-reactive polypeptides, as indicated above, and selecting those antibodies specific to the cross-reactive polypeptides using techniques that are well known to those skilled in the art. These antibodies can detect the presence of cross-reactive protein by a variety of immunoassay techniques. The nucleotide probe sequences provided by the invention can be used to detect expression of mRNA corresponding to cross-reactive proteins in accordance with any of the standard techniques. Expression may be detected either by in situ hybridization or by extraction and detection of mRNA. The particular procedures for gene probe assays and immunoassays will be well-known to those skilled in the art.

Immunoassays

The antibodies of the present invention can be used to detect epitopes found on proteins cross-reactive with a peptide according to SEQ ID NO. 1 but not found on haptoglobin 1 or haptoglobin 2 in histological sections of breast cancer tissue as well as in other solid tumors such as, lung cancer tissue, genito-urinary tumor tissue and gastrointestinal tumor tissue. It has been found that the presence of such epitopes in breast cancer tissue correlates with a worsened prognosis; it indicates that the cancer will probably recur early and metastasize early, compared to those whose tissues are negative for Hpr epitopes. Breast tissues in which such epitopes are found are characterized by three qualities: the immunoreactivity is present in infiltrating breast carcinoma; granular cytoplasmic immunoreactivity is observed without nuclear staining; and the staining is heterogeneous, i.e., there is cell-to-cell or region-to-region variability.

One can detect antibody binding to tissue sections by any detection means known in the art for example, a radiolabel or a stain. A particularly useful stain employs peroxidase, hydrogen peroxide and a chromogenic substance such as aminoethyl carbazole. The peroxidase (a well known enzyme available from many sources) can be coupled to an anti-Hpr antibody or merely complexed via one or more antibodies to an antibody which specifically binds a protein which is cross-reactive with a peptide according to SEQ ID NO. 1. For example, a goat anti-peroxidase antibody and a goat anti-Hpr antibody can be complexed via an anti-goat IgG. Such techniques are well known in the art. Other chromogenic substances and enzymes may also be used. Radiolabeling of antibodies may also be used to detect antibody binding to sections. Labeled antibodies may be anti-Hpr or second antibodies immunoreactive with anti-Hpr antibodies. Again, such techniques are well known.

The precise technique by which a protein cross-reactive with the hpr gene product is detected in breast cancer patients is not critical to the invention. Biochemical or immunological techniques can now be used which do not employ immunohistochemistry, although that is the preferred method of the present invention. Solution assay methods, including calorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate proteins cross-reactive with a peptide according to SEQ ID NO. 1 in a patient by preparing an extract of a tissue sample from the patient and assaying the extract.

A protein cross-reactive with the hpr gene product can be quantitated in a biological fluid, such as serum, plasma, effusions, ascites, urine, cerebrospinal fluid, semen, breast aspirates and fluids of ovarian origin, using any protein detection means known in the art. Preferred methods employ immunological detection means. These include: radioimmunoassay, enzyme linked immuno-adsorbent assay, complement fixation, nephelometric assay, immunodiffusion or immunoelectrophoretic assay and the like. Plasma should be anti-coagulated before use, as is known in the art. Cellular elements and lipid may be removed from fluids, e.g., by centrifugation. For dilute fluids, such as urine, protein may be concentrated, e.g., by ultra-filtration or salting-out.

One preferred method of detecting and/or quantitating a protein cross-reactive with the hpr gene product in fluid samples employs a competitive assay. An antibody immunoreactive with an epitope found on a protein cross-reactive with Hpr protein but not found on Hp1 and Hp2 is attached to a solid support such as a polystyrene microtiter dish or nitrocellulose paper, using techniques known in the art. The solid support is then incubated in the presence of the fluid to be analyzed under conditions where antibody-antigen complexes form and are stable. Excess and unbound components of the fluid are removed and the solid support is washed so that antibody-antigen complexes are retained on the solid support. A fixed amount of a polypeptide containing an epitope bound by the antibody attached to the solid support is then incubated with the solid support. The polypeptide binds to any unbound antibody which is attached to the solid support. The polypeptide has been conjugated to a detectable moiety, such as biotin, peroxidase or radiolabel, by means well known in the art. Excess and unbound polypeptide is removed and the solid support is washed, as above. The detectable moiety attached to the solid support is quantitated. Since any cross-reactive protein in the sample and the polypeptide have competed for the same antibody binding sites, the cross-reactive protein in the fluid can be quantitated by its diminution of the binding of the polypeptide to the solid support. Antibodies employed in this assay may have absolute immunoreactive specificity for a protein cross-reactive with a peptide according to SEQ ID NO. 1 but not react with Hp1 or Hp2. Alternatively, relatively specific antibodies may be used under conditions which destabilize immunoreactivity with Hp1 and Hp2. Polyclonal antibodies which contain an antibody species immunoreactive with an epitope on Hpr protein but not on Hp1 or Hp2, may also be used.

Although this assay has been described with particularity to the hpr system, it can also be used to quantitate other protein analytes in biological fluids. That is, a detectably labeled polypeptide which shares an epitope with a protein analyte can be used to quantitate the analyte. A monospecific antibody is not required as the specificity is provided to the assay by means of the polypeptide.

Nucleotide Probe Assays for Expression

The nucleic acid probes described above for use in screening gene libraries and selecting clones may also be used to detect mRNA transcripts in tumor cells that express a protein cross-reactive with the hpr gene product. These probes preferably correspond to a sequence which encodes portions of the distinct sequences of OA-519 (see FIGS. 12D). The probe can be either single or double stranded DNA or RNA. The size of a probe can vary from less than approximately 20 nucleotides to hundreds of nucleotides. The most desirable nucleotide probes do not detect nucleotide sequences unrelated to their intended target, do not show significant homology with unrelated nucleotide sequences, and do not contain complementary sequences such that they would self-hybridize or fold upon themselves. The guanine and cytosine content of desirable probes is not so high as to promote non-specific hybridization with unrelated sequences rich in guanine and cytosine. Finally, the melting temperature and free energy of binding are generally favorably suited to the detection technique for which they are intended. The probe may be radio-labeled, labeled with a fluorescent material, a biotinylated nucleotide, or the like. Procedures for the preparation and labeling of nucleotide probes are well known in the art.

In situ hybridization of nucleotide probes to tissue sections is performed using standard methods, as described by, e.g., Baldino, et al., *Methods in Enzymol.*, 1989, vol. 168, p. 761–77; Emson, et al., *Methods in Enzymol.*, 1989, vol. 168, p. 753–61; Harper, et al., *Methods in Enzymol.*, 1987, vol. 151, p. 539–51; Angerer, et al., *Methods in Enzymol.*, 1987, vol. 152, p. 649–61; Wilcox, et al., *Methods in Enzymol.*, 1986, vol. 124, p. 510–33, incorporated herein by reference, using nucleotide probes described above. One preferred method for detecting MRNA associated with expression of the cross-reactive protein is in situ hybridization to tissue sections taken from tumors. Detection of hybridization by a probe having a nucleotide sequence corresponding to the amino acid sequence of OA-519 in the cytoplasm of tumor cells indicates expression by that cell of mRNA corresponding to a protein cross-reactive with the hpr gene product. Tissue sections are prepared as for immunohistochemistry.

Alternatively, extracts of RNA from tissue samples can be analyzed for the presence of sequences encoding the proteins of this invention. The diagnostic test employing a nucleotide probe will employ a biological sample from an individual. Nucleic acids are recovered from the sample employing standard techniques well known to those skilled in the art. The nucleic acid then is incubated with the probe and hybridization is thereafter detected. The presence of a nucleic acid whose sequence corresponds to that of the probe is preferably detected by Northern blot, or slot/dot blot.

Alternatively, a nucleic acid whose sequence corresponds to the sequence of OA-519 may be detected in the RNA extract of tumor tissue by nucleic acid amplification, using primers corresponding to the nucleic acid sequence of OA-519, (see methods reviewed in Van Brunt, BioTechnology, 8:291–294, 1990). Similar primers can be used to amplify genomic DNA sequences encoding OA-519. The preferred method of amplification uses the polymerase chain reaction (PCR). Primers can be constructed corresponding to unique portions of the nucleic acid sequence of OA-519, determined as described above for nucleic acid probes. Using these primers, RNA or DNA in a nucleic acid extract of tumor tissue will be amplified by PCR only if it contains the unique OA-519 sequences.

An elevated level of OA-519 mRNA in a cell corresponds to elevated FAS protein expression by the cell, and OA-519 mRNA can be quantitated in a number of ways. Using Northern blotting or dot hybridization, purified RNA samples of known concentration and integrity can be hybridized with labeled OA-519 probes. For each sample, the signal which is obtained can be compared ratiometrically to the signal obtained when the same sample is hybridized to a labelled probe for a constitutively expressed gene whose expression does not vary from cell to cell or sample to sample. Comparison of the ratios between different samples permits estimation of the differences in OA-519 levels.

Alternatively, the level of OA-519 mRNA expression can be estimated by quantitative polymerase chain reaction. Using primers whose sequences correspond to the OA-519 nucleotide sequence, cDNA can be synthesized initially using reverse transcriptase, then the resultant cDNA amplified according to the polymerase chain reaction. The reaction is run under conditions and terminated so as to produce amounts of amplified products in proportion to the amount of mRNA originally present in the sample. The amount of product can be quantitated by ethidium fluorescence in comparison to known standards following electrophoresis, or by dot hybridization with labeled probes. Expression of constitutively expressed genes can be measured as a control, permitting standardized comparison of results, such as with the previously described hydridization reactions. Treatment of samples with ribonuclease A or other RNAses in control samples prior to amplification verifies that the signal is derived soley from RNA.

Elevated levels of a protein cross-reactive with a peptide according to SEQ ID NO. 1 (e.g., OA-519) in a sample, such as the blood or other biological fluid, from a patient correlates with proliferation and likely metastasis of breast cancer as well as other solid tumors. Other tumors include lung cancer, genito-urinary tumors, and gastrointestinal tumors. The determination of elevated levels of a protein cross-reactive with a peptide according to SEQ ID NO. 1 is done relative to a patient with no detectable solid tumor. This may be the same patient or a different patient. For example, a first sample may be collected immediately following surgical removal of a solid tumor. Subsequent samples may be taken to monitor recurrence of tumor growth and/or tumor cell proliferation. Determination of the elevated level of cross-reactive protein may be done by direct detection of the protein or by indirect detection of its expression via measurement of mRNA encoding the protein. The detection may be in tissue sections by immunohistochemistry or in situ hybridization or it may be in extracts of tissue samples by solution immunoassay, or mRNA hybridization or amplification. In addition, the assay of a protein cross-reactive with a peptide according to SEQ ID NO. 1 in biological fluids can be used to distinguish between neoplastic and non-neoplastic fluid accumulations in patients carrying a malignant diagnosis.

The diagnostic methods of this invention are predictive of proliferation and metastatic potential in patients suffering from breast carcinomas including lobular and duct carcinomas, and other solid tumors, carcinomas, sarcomas, and cancers including carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage. Cells of these tumors which express a protein cross-reactive with the hpr gene product but not with Hp1 or 2 are aggressive tumor cells and result in decreased survival, increased metastasis, increased rates of clinical recurrence and overall worsened prognosis.

The following examples are not intended to limit the invention, but merely provide specific embodiments which can be employed.

EXAMPLES

Example 1

This example describes the isolation and purification of Hpr protein from human pregnancy plasma, and the separation of the two subunits.

Maternal plasma from third trimester pregnancies was obtained from discarded EDTA-anticoagulated whole blood samples. The plasma was stored at −70° C. until use.

Proteins reactive with the whole IgG fraction of a rabbit antiserum to pregnancy-associated plasma protein A (PAPP-A) (Dako Laboratories, Santa Barbara, Calif.) were purified by successive chromatographic steps. The purification was monitored by optical density of chromatographic effluents at 280 nm, and analysis of fractions using Coomassie-stained Laemmli gels, and Western blotting. Initially, 80 ml of plasma was loaded onto a 2.5×30 cm CIBACRON BLUE F3G-A SEPHAROSE (Pharmacia) column equilibrated in 50 mM sodium phosphate, pH 6.8 at 4° C. The flow-through containing all the detectable immunoreactive material was dialyzed against 20 mM sodium phosphate, pH 6.8 at 4° C. with 1 mM NaN$_3$, and applied to 2.5×10 cm column of DE-52 DEAE-cellulose (Pierce Chemical Co.) equilibrated in the same buffer. The immunoreactive material was eluted with 0.2M NaCl in the starting buffer. The eluate was dialyzed against 20 mM Tris-HCl, pH 8.5 at 4° C. containing 0.15M NaCl, 1 mM beta-mercaptoethanol, and 1 mM NaN$_3$, then loaded onto a 2.5×60 cm column of FAST FLOW Q-SEPHAROSE (Pharmacia, Piscataway, N.J.) equilibrated in the same buffer. The column was eluted with a 500 ml linear gradient of 150 mM to 500 mM NaCl at a flow-rate of 100 ml/hr at 4° C. The immunoreactive protein species eluted in the range between 0.25 and 0.28M NaCl. The fractions containing immunoreactive protein were pooled and dialyzed against 200 mM Tris-acetate, pH 7.5 at 4° C. with 1 mM beta-mercaptoethanol and 1 mM NaN$_3$ and applied to a 5×90 cm SEPHAROSE CL4B (Pharmacia) column.

FIG. 1 summarizes the purification of the dominant immunoreactive bands recognized by the polyspecific anti-PAPP-A (Dako). The figure shows a Coomassie stained 10–15% Laemmli gel (Nature, vol 227, pp. 680–685, 1970) and corresponding Western blot. Western blotting was carried out essentially according to published procedures. Following NaDodSO$_4$ polyacrylamide gel electrophoresis, protein was transferred to 0.45 u nitrocellulose sheets (Schleicher & Schuell) in 96 mM glycine, 12.5 mM Tris, 0.1% NaDodSO$_4$, and 20% methanol at 40 V, 250–300 mA, at 4° C. for 6 hrs. After evaluating transfer efficiency by Ponceau S staining, the membranes were blocked with 3% bovine serum albumin, then incubated sequentially with anti-PAPP-A antibody for 2 h and protein A labeled with $^{125}$I for 1 h (Gershoni, et al., *Analyt. Biochem., vol.* 131, pp. 1–15, 1983). Washes after each step were performed in Tris-saline containing 1 mM NaN$_3$.

Sequential chromatographic steps involved removal of albumin and additional protein species on CIBACRON BLUE F3GA SEPHAROSE, (Lane a), step elution from a DEAE cellulose column (Lane b), gradient elution from a FAST-FLOW Q SEPHAROSE anion exchange column (Lane c), and gel permeation chromatography on SEPHAROSE CL-4B (Lane d). Interestingly, gel filtration incompletely resolved the immunoreactive proteins into three consecutively-eluting species consisting of the 40 kDa species co-eluting with the weakly reactive 20 kDa species, the 40 kDa band co-eluting with a weakly immunoreactive 16.5 kDa species, and lastly, as a separate, albeit overlapping peak, the 40 kDa species co-eluting with strongly immunoreactive 16.5 kDa band. (Molecular weights reported herein generally refer to the molecular weight determined by SDS-PAGE.)

To separate the individual immunoreactive chains under denaturing conditions, fractions containing immunoreactive protein were pooled and dialyzed against 20 mM Tris-HCl, 6M urea, 10 mM beta-mercaptoethanol, pH 8.5 at 25° C. (dialysis was performed at 4° C., but the pH was adjusted to be 8.5 at the indicated temperature). The final purification step utilized HPLC on a Waters system with a 5×50 mm MONO Q HR5/5 (Pharmacia) column monitored at 280 nm. The sample was injected in the Tris-urea-mercaptoethanol starting buffer and following 10 ml of isocratic flow at 2 ml/min, a linear gradient of 30 ml over 15 min was applied to final conditions of starting buffer with 0.5M NaCl.

Figure 2:
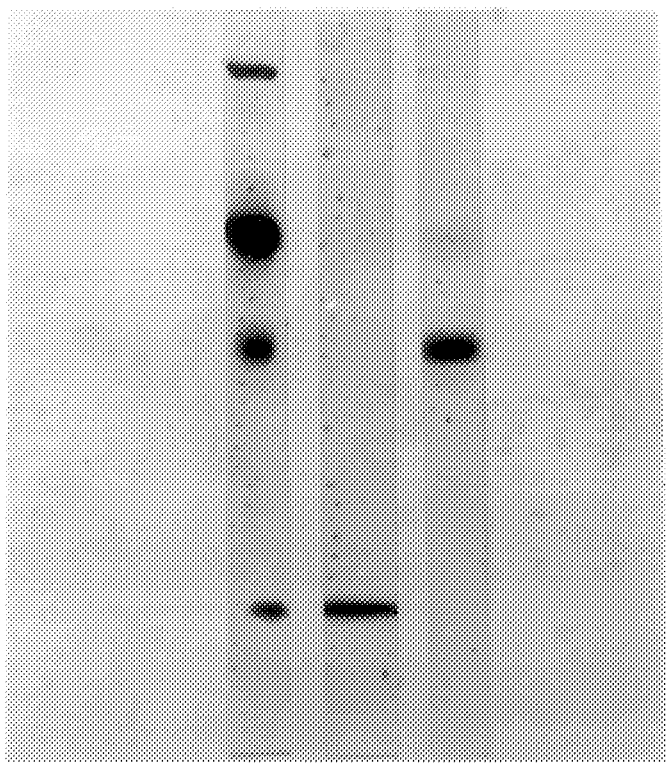
FIG. 2 shows a polyacrylamide gel electrophoretic separation of immunoreactive heavy and light chains by gradient anion exchange chromatography.
Figure 7A:
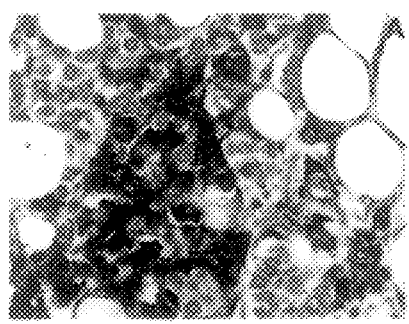
FIG. 7, Panel A shows immunohistochemical staining of human breast cancer cells using antibodies raised against a synthetic peptide whose sequence corresponds to the hpr gene. Panel B shows the same experiment except that the antibody was pre-incubated with purified Hpr protein from pregnancy serum. Panel C shows staining with anti-CEA, which was not abolished by preincubation with Hpr protein (Panel D).
Figure 7B:
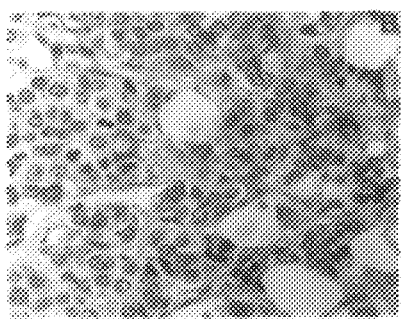
Figure 7C:
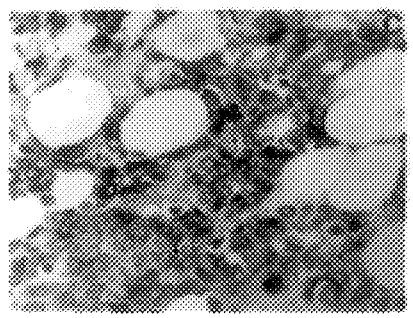
Figure 7D:
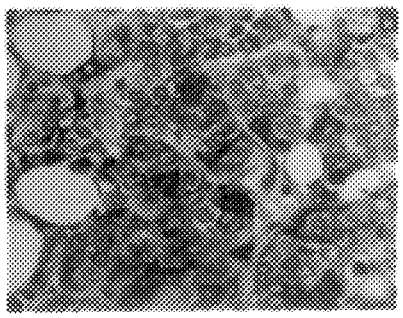

A Coomassie blue stained 10% Laemmli gel showing the separation of immunoreactive heavy and light chains by gradient anion exchange chromatography on MONO Q HR5/5 using HPLC is shown in FIG. 2. Lane a is 100 ug of purified immunoreactive protein. Lane b contains the alpha chains, which flowed through in the void volume, while lane c contains the immunoreactive 40 kDa chain which eluted in 0.85M NaCl. Fractions containing the 40 kDa species were pooled, dialyzed against 0.2M NH$_3$HCO$_3$ buffer and lyophilized.

Example 2

This example demonstrates that a 20-amino acid stretch of the heavy chain (beta chain) of Hpr protein is 100% homologous to the beta chains of haptoglobin 1 and 2.

The lyophilized samples of the 40 kDa species made according to Example 1 were dialyzed against three changes of 0.2M NH$_4$HCO$_3$ and lyophilized, then thrice re-lyophilized from HPLC-grade water. Gas phase sequencing was carried out. Samples of intact protein chains generally consisted of 100 ug of protein as determined by Lowry assay (J. Biol. Chem., vol. 193, pp 265–275, 1951). Peptide samples generally consisted of 0.5–2 nanomoles as quantitated by the sequencer. Protein was sequenced on an APPLIED BIOSYSTEMS MODEL 470A SEQUENATOR equipped with on-line phenylthiohydantoin (PTH) analysis using the regular program O3RPTH. The PTH derivatives were separated by reversed phase HPLC over an APPLIED BIOSYSTEM 200×21 mm C-18 column.

N-terminal sequencing yielded twenty residues shown in FIG. 3. Using the protein sequence database of the National Biomedical Research Foundation and the DFASTP alignment program three protein sequences showed 100% homology over the entire 20 amino acid stretch: the beta-chain of human haptoglobin 1; the beta-chain of human haptoglobin 2; and the predicted beta-chain of haptoglobin-related protein precursor.

Example 3

This example demonstrates that the haptoglobin-type protein isolated from pregnancy serum according to Example 1 differs from Hp1 and 2 in its 16.5 kDa chain.

Although sequence analysis placed the pregnancy plasma protein unequivocally in the haptoglobin (Hp) gene family, more specific assignments could not be made, since the N-terminal sequence for the beta-chains of all species is identical. FIG. 4 shows the results of an immunologic analysis performed with purified Hp1 and 2 standards, the haptoglobin-type protein purified from pregnancy serum, rabbit anti-haptoglobin and the anti-PAPP-A. Panel A shows a 10–15% Coomassie stained Laemmli gel of Hp1, Hp2, and the haptoglobin-type protein purified from pregnancy serum (lanes a–c, respectively). Panel B is a corresponding immunoblot with anti-haptoglobin, 1:50; panel C is an immunoblot with anti-PAPP-A, 1:50.

Anti-haptoglobin reacts strongly with all the 40 kDa beta chains, and Hp1 and 2 alpha chains; the 16.5 kDa band from lane c containing the purified protein is only weakly reactive. In contrast, anti-PAPP-A, while strongly labeling the 40 kDa beta chains, reacts weakly with Hp2 alpha chain and is only slightly reactive with Hp1 alpha chain. The 16.5 kDa band from the purified protein in lane C is disproportionately intense in comparison to its Coomassie staining, particularly when compared to the disproportionately weak relative immunoreactivity of the Hp1 alpha chain shown in lane a. Thus, the alpha chain isolated from pregnancy plasma is immunologically distinct, containing epitopes seen by the anti-PAPP-A which are not present in either the Hp1 or Hp2 alpha chains.

Example 4

This example demonstrates that there are sequence differences between the alpha chain of Hpr protein and those of Hp1 and Hp2. In addition, the difference seen is consistent with the assignment of the haptoglobin from pregnancy serum as being the hpr gene product.

Peptide mapping was performed using the Elder technique (Speicher, et al. *Proc. Natl. Acad. Sci. U.S.A.*, vol. 77, pp 5673–5677, 1980; and Elder, et al., *J. Biol. Chem.*, vol. 252, pp 6510–6515, 1977). Briefly, slices containing the desired proteins were exercised from Coomassie-stained gels, exhaustively radioiodinated, and enzymatically digested with trypsin. The resultant limit peptides were then subjected to high-voltage electrophoresis along one dimension of a cellulose sheet, followed by ascending partition thin layer chromatography in the perpendicular dimension.

Peptide mapping by this technique detects only tyrosine-containing peptides. Using the published amino acid sequences, the family of tryptic peptides from the chains of Hp1 and Hp2 should each be similar, since Hp2 resulted from a partial reduplication of Hp1 (FIGS. 5a and 5c). The principal differences in amino acid sequence between Hpr protein, Hp1 and Hp2 lie in the alpha chains. Within the alpha chains, these differences cluster principally at the N-termini. With reference to peptide mapping, using the deduced hpr gene alpha chain sequence one would predict the same tryptic peptides as obtained from Hp1 plus one additional tyrosine-containing peptide. FIG. 5b shows the peptide map of the purified protein alpha chain with an arrow highlighting the one additional peptide obtained experimentally. These results thus suggest that the unique haptoglobin-type protein purified from pregnancy plasma is the hpr gene product. FIG. 5d is a mixing experiment where Hp1 and the purified protein alpha chain were mixed before mapping. Again, the additional peptide is present but with less relative intensity, while the shared peptides all co-migrate.

Example 5

This example demonstrates that the alpha chain of the haptoglobin-type protein from pregnancy serum shares epitopes with a synthetic peptide made according to the deduced Hpr protein sequence.

A synthetic peptide corresponding to the 34 N-terminal residues of the predicted hpr gene product (Maeda et al., *Proc. Natl. Acad. Sci. U.S.A.*, vol. 83 pp.7395–7399, 1986) was synthesized on an Applied Biosystems Model 43A peptide synthesizer by the solid phase method of Merrifield (*J. Am. Chem. Soc.*, vol. 85, pp. 2149–2154, 1968). Because histidine coupling can be inefficient, lysine was conservatively substituted for the histidine in position 28.

Two separate columns were made using beads coupled to: haptoglobin 1, and the 34-mer synthetic peptide. Haptoglobin 1 (Hp1) and the Hpr synthetic peptide were immobilized using agarose beads derivatized with 1,1-carbonyldimidazole (Reacti-Gel 6X, Pierce) which results in a stable N-alkylcarbamate linkage. 5 ml of gel was washed with 0.1M borate and 0.15M NaCl, pH 8.5, at room temperature (RT) to remove the acetone. 4 mg of Hp1 (Sigma) diluted to 1 mg/ml in borate buffer, and 50 mg Hpr synthetic peptide diluted to 12.5 mg/ml in borate buffer were each added to 5 ml of gel and incubated with agitation at 4° C. for 30 hr. After incubation, the supernate was decanted and an equal volume of 0.2M Tris was added to quench any remaining reactivity. The gels were then extensively washed with Tris-saline buffer. The Hpr peptide column was then denatured with 100 ml of 0.1% NaDodSO$_4$ in Tris-saline buffer.

Anti-Hpr antibodies reactive with the Hpr peptide were isolated from the crude anti-PAPP-A serum by means of sequential affinity chromatographic steps. First, 100 ul of crude anti-PAPP-A antibody in 10 ml Tris-saline buffer was incubated with the Hp1 gel overnight at 4° C. with agitation. The gel was next washed extensively with Tris-saline and the flow-through collected over a 5 ml hydroxyapatite column. Antibodies reactive with the Hp1 column were eluted with 20 ml of acetate buffer (0.05M sodium acetate, 0.15M NaCl, pH 3.5, at room temperature). The antibodies which flowed through the column were eluted from the hydroxyapatite column with 20 ml of 0.4M sodium phosphate. Both sets of antibodies were dialyzed against 2 l of Tris-saline buffer.

The antibodies unreactive with the Hp1 column were then incubated with the denatured Hpr peptide gel overnight at 4° C. with agitation. Antibodies reactive with the Hpr peptide were eluted with 20 ml of acetate buffer and dialyzed against Tris-saline. Each of these antibody fractions were used to label immunoblots of 10–15% gradient Laemmli gels on which the subunits of haptoglobin 1 and the haptoglobin-type protein from pregnancy serum (according to Example 1) were separated by electrophoresis.

FIG. 6, panel A shows a Coomassie stained 10–15% gradient Laemmli gel of 25 ug Hp1 in the left lane, and 100 ug Hpr protein on the right. Panels B–E are immunoblots of the same protein loads. Panel B was incubated with unabsorbed anti-PAPP-A antibody, 1:50. Panel C was incubated with the subset of anti-PAPP-A antibodies which bound to immobilized Hp1; panel D was incubated with the unreactive antibodies which flowed through. Note the enrichment for antibodies to the 40 kDa beta chains which bound to the Hp1 gel in panel C; while antibodies to the unique immunoreactive alpha-chain were unreactive with immobilized Hp1 and flowed through (panel D). Panel E was incubated with the subset of antibodies seen in panel D which reacted with immobilized, denatured, synthetic Hpr peptide. Note that these antibodies, which bound to the synthetic Hpr peptide, react only with the 16.5 kDa alpha chain of the pregnancy serum associated haptoglobin-type protein. This demonstrates that the unique alpha-chain of this protein contains Hpr epitopes.

Example 6

This example shows that Hpr epitopes are identified in the cytoplasm of human breast carcinoma.

Paraffin embedded human breast carcinoma specimens were obtained from the files of the Department of Pathology of the Johns Hopkins Hospital. Buffered 10% formalin-fixed, paraffin embedded 6 u tissue sections were deparaffinized in xylene, and rehydrated in alcohol-water baths, then incubated in Tris-saline at pH 7.6, followed by blocking of endogenous peroxidase activity with 3 % H$_2$O$_2$ for 15 min. After Tris-saline washes, sections were blocked with normal swine serum diluted 1/100 (Dako) for 30 min, followed by incubation with specific antibody or non-immune serum overnight at 4° C. After washing in Tris-saline, swine-anti-rabbit immunoglobin IgG fraction (Dako), 1/100 in 0.5M tris buffer was applied for 30 min, followed by a peroxidase-rabbit-anti-peroxidase complex (Dako). After final washing, the slides were incubated with diaminobenzidine (Sigma) substrate for 6 min, counterstained in Mayer's hematoxylin, coverslipped, and examined.

Antibodies were raised against Hpr protein by immunization of rabbits with the 34-mer synthetic peptide described above in Example 5. For purposes of immunization, the peptide was conjugated to keyhole limpet hemocyanin (KLH) (Boehringer Mannheim) essentially as described (Lerner, et al., Proc. Natl. Acad. Sci. U.S.A., vol. 78, pp. 3403–3407, 1981). 8 ul of an 8.75 mM solution of malemidobenzoyl-n-hydroxysuccinimide (MBS) (Pierce Chemical Co.) in dimethyl formamide were added to 14.8 mg of KLH in phosphate-buffered saline and incubated at room temperature for 30 min. The KLH-MBS conjugate was separated from unreacted MBS by gel filtration on a Pharmacia PD-10 column. 1.2 mg of Hpr peptide was added directly to the KLH-MBS and mixture incubated a further 30 min at room temperature. To estimate coupling efficiency, a 35 ul sample of the unfractionated 3.0 ml reaction volume was chromatographed on a Pharmacia Superose 12 column using a Waters HPLC at 1 ml/min in PBS and the effluent monitored at 214 nm. Unreacted peptide was quantified by peak integration and comparison to standards of peptide run alone. This method yielded an approximate substitution ratio of 4.6 peptides per KLH molecule.

Two Pasteurella-free New Zealand White rabbits (Dutchland) were each inoculated on Day 0 with 200 ug of antigen in 1 ml of an emulsion comprised of equal parts of phosphate buffers saline (PBS) and complete Freund's adjuvant; the inoculae were divided among 34 subcutaneous and intramuscular sites. On Day 14, the animals were boosted with similar amounts of antigen in incomplete Freund's adjuvant. The rabbits were test bled on Day 32; serum from the positive rabbit was collected over the ensuing month.

Bovine serum albumin was derivatized with the synthetic Hpr peptide as described above. An enzyme-linked immunosorbent assay was performed as described by (Voller et al., J. Clin. Pathol., vol. 31, pp. 507–520, 1978) using 2 ug of BSA-peptide per well which was tested against dilutions of rabbit serum and developed with protein A-horseradish peroxidase conjugate and o-phenylene-diamine substrate.

To purify the antibody, a 10 cm×5 mm SELECTISPHER-10 activated tresyl column HPLC affinity column (Pierce Chemical Co.) was derivatized with the Hpr synthetic peptide. The column was washed with 30 ml PBS at a flow rate of 2 ml/min, then 27 mg of peptide dissolved in 4.5 ml of PBS was passed through the column at a flow rate of 1 ml/min. Unreacted tresyl groups were capped by passing 30 ml of 0.2M Tris HCl, pH 8.0 through the column. For antibody purification, the column was equilibrated in 300 mM NaCl, 20 mM sodium phosphate, pH 7.5 at room temperature. 10–20 ml serum were loaded onto the column at a flow rate of 0.5 ml/min. After loading, the column was washed with buffer until the optical density of the effluent at 280 nm returned to zero. Antibody was then eluted with 6M urea in the same buffer, and the antibody-containing fractions immediately dialyzed into Tris-buffered saline containing 1 mM $NaN_3$.

FIG. 7 illustrates immunoperoxidase staining of a primary breast adenocarcinoma with both anti-Hpr antibody (Panel 7a) and anti-CEA antibody (Panel 7c); note the intense cytoplasmic positivity of anti-Hpr staining. When anti-Hpr antibody was incubated for 2 hr at 4° C. with native Hpr protein, positive cytoplasmic staining was abolished (Panel 7b). To establish specificity of the immunoabsorption, anti-carcinoembryonic antigen (CEA) antibodies were incubated under similar conditions with native Hpr protein. The cytoplasmic CEA positivity was not abolished by such pre-incubation with Hpr protein (Panel 7d). Together with the failure of Hp1 and Hp2 to inhibit staining, this establishes that epitopes derived from the N-terminus of the predicted alpha chain of the hpr gene product can be detected in human breast carcinoma. Thus Hpr protein, a modified form of Hpr, or a highly cross-reactive protein must be present in human breast carcinoma cells.

Example 7

This example demonstrates that there is a correlation between expression of a protein cross-reactive with the hpr gene product by human breast cancer and the time interval that a patient remains disease-free.

Sixty-one cases of human breast cancer were available for concurrent evaluation of cancer-related antigen expression and immunoreactivity with anti-PAPP-A antiserum. Expression of a protein cross-reactive with the hpr gene product was evaluated by immunohistochemical staining of paraffin-embedded material using affinity-purified polyclonal antibody to a synthetic peptide whose sequence was derived from the hpr gene sequence. PAPP-A positivity was similarly evaluated using anti-PAPP-A antiserum. Of the 61 patients, 40 had Stage I disease (tumor less than 5 cm, negative lymph nodes) and 21 had Stage II disease (tumor less than 5 cm, positive axillary lymph nodes). Data were analyzed in a life table format using the BMDP Statistical Program. Two statistical tests, the Generalized Wilcoxon (Breslow), and the Generalized Savage (Mantel-Cox) were used to determine the significance of the differences between curves.

Figure 8:
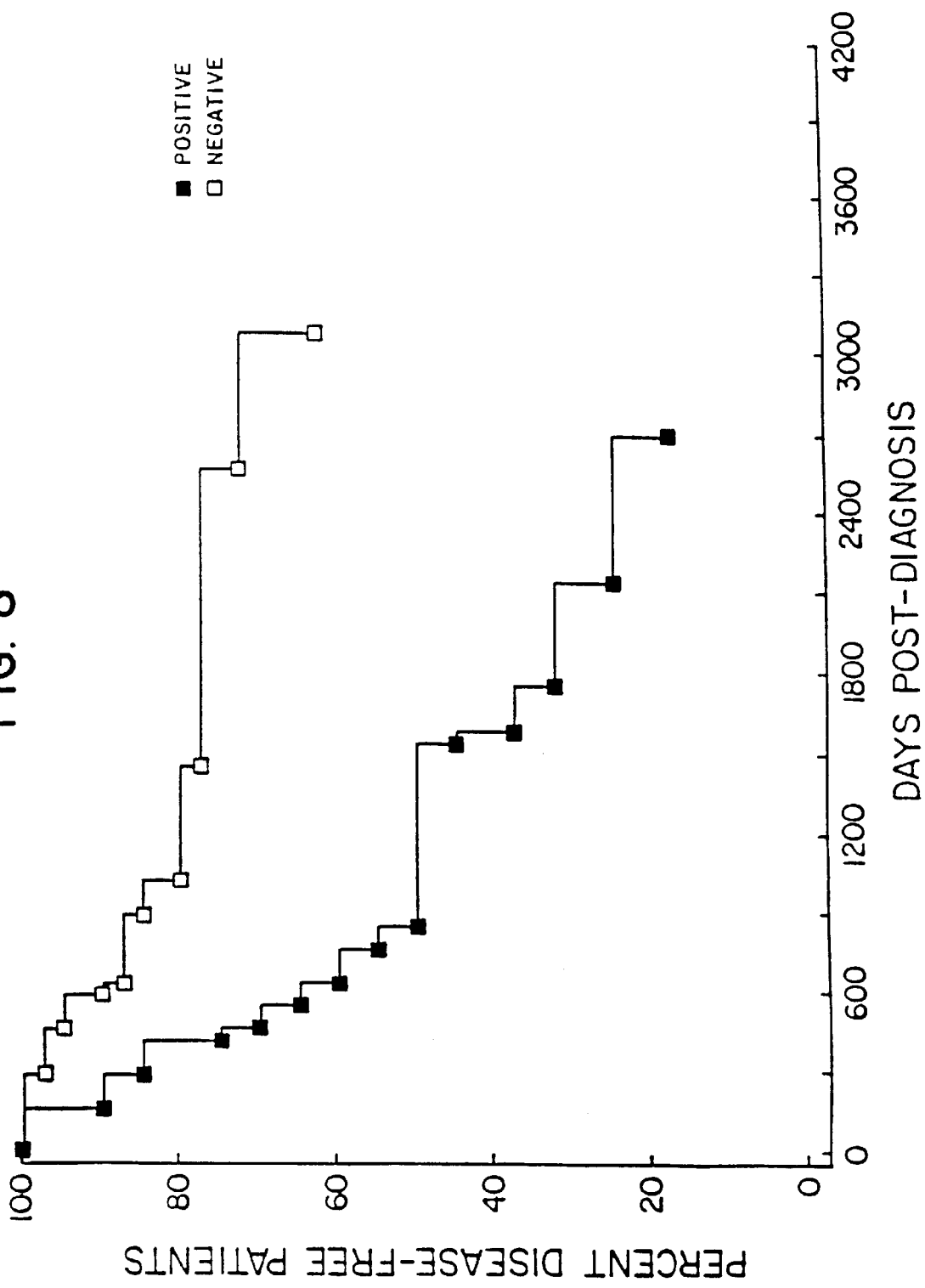
FIG. 8 shows the correlation of immunochemical staining using Hpr-specific antibodies with relapse of breast cancer.

The results are shown in FIG. 8. The ordinate shows the percentage of patients remaining disease-free, while the abscissa shows the time interval since diagnosis. The differences between the curves are highly significant, with p less than 0.0005 (Wilcoxon) and p less than 0.0003 (Savage).

Example 8

This example demonstrates that cultured breast cancer cells express a protein cross-reactive with the hpr gene product.

Although fresh human breast carcinoma can be used as a source of a protein cross-reactive with the hpr gene product, the quantities are generally small, and availability is irregular. For these reasons, a series of human breast carcinoma cell lines were obtained from the American Type Culture Collection (Rockville, Md.) and screened for expression of a protein cross-reactive with the hpr gene product by an immunohistochemical procedure. FIG. 9 shows the results of this approach in one such line, MDA-MB-231, an estrogen receptor negative cell line (Anderson, J. Submicroscop. Cytol., vol. 16, pp 673–690, 1984).

Briefly, cells were grown on chamber slides in L-15 medium supplemented with 10% fetal bovine serum and antibiotics, fixed in paraformaldehyde, permeabilized with Triton X-100, incubated with anti-Hpr 40 ug/ml, or controls overnight at 4° C., and developed sequentially with a biotinylated secondary antibody, avidin-peroxidase, and aminoethyl-carbazole-peroxide substrate solution.

Figure 9A:
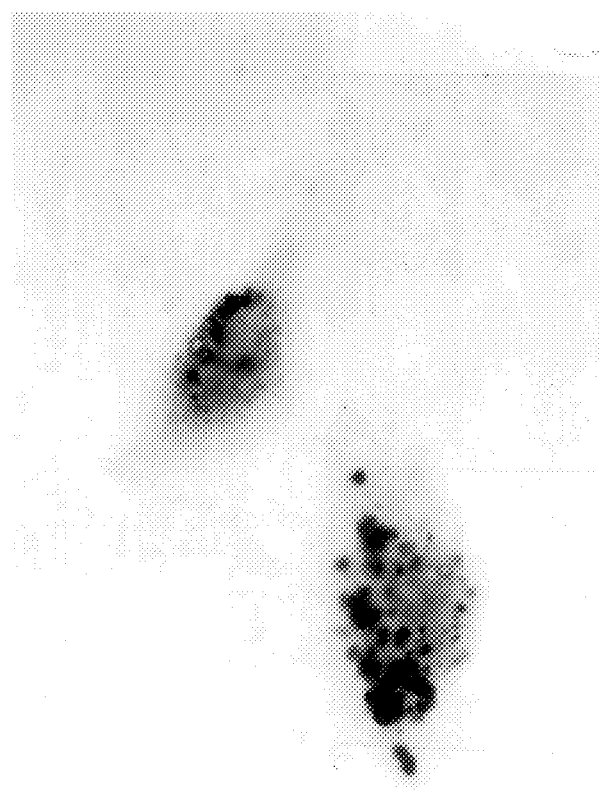
FIGS. 9A and B show the staining of a breast cancer cell line with antibody raised against a synthetic peptide made according to the sequence of the hpr gene.
Figure 9B:
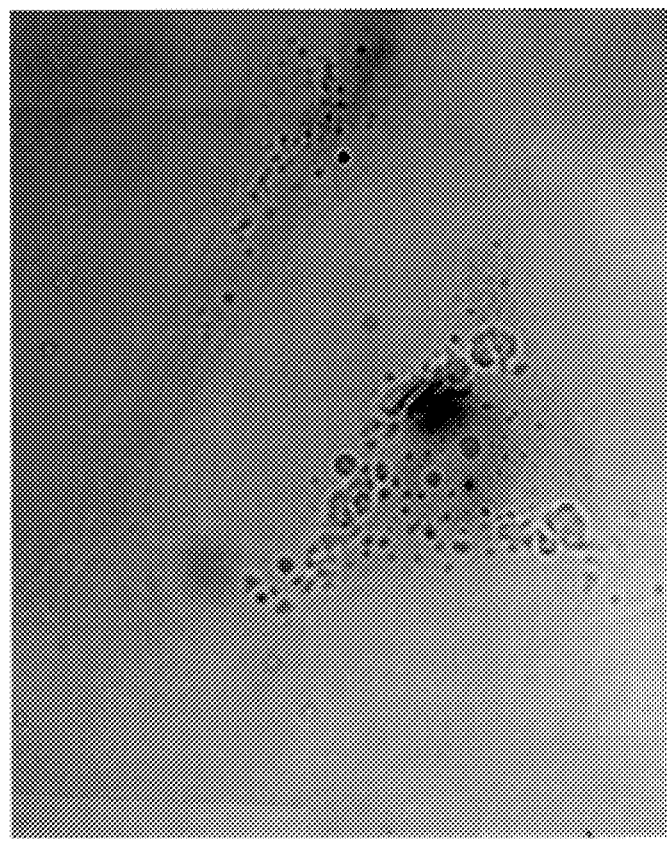

FIG. 9A shows granular cytoplasmic staining by the specific antibody, while FIG. 9B shows the control without primary antibody; unrelated affinity-purified antibodies stain with appropriate distributions when used as unrelated positive primary antibody controls in this method. Thus, it can be readily seen that these cultured cells can produce a protein which is cross-reactive with the hpr gene product.

Example 9

This example shows that decidua tissue synthesizes a protein which is cross-reactive with the hpr gene product under physiologic conditions.

Because a protein which is cross-reactive with a peptide according to SEQ ID No. 1 is purified from pregnancy serum, pregnancy-specific tissues were screened immuno-histochemically for expression. Fresh decidua was obtained from tissues otherwise to be discarded following elective abortions and was formalin-fixed. Buffered 10% formalin-fixed, paraffin embedded 6 u tissue sections were deparaffinized in xylene, and rehydrated in alcohol-water baths, then incubated in Tris-saline at pH 7.6, followed by blocking of endogenous peroxidase activity with 3% $H_2O_2$ for 15 min. After Tris-saline washes, sections were blocked with normal swine serum diluted 1/100 (Dako) for 30 min, followed by incubation with specific antibody made as described above in Example 6, or for control, with nonimmune serum overnight at 4° C. and developed sequentially with a biotinylated secondary antibody, avidin-peroxidase, and aminoethyl-carbazole-peroxide substrate solution. The slides were incubated with diaminobenzidine (Sigma) substrate for 60 min, counterstained in Mayer's hematoxylin, coverslipped, and examined.

Figure 10A:
FIGS. 10A and B show the staining of decidua with polyclonal antibodies raised against the synthetic peptide made according to the predicted sequence from the hpr gene.
Figure 10B:
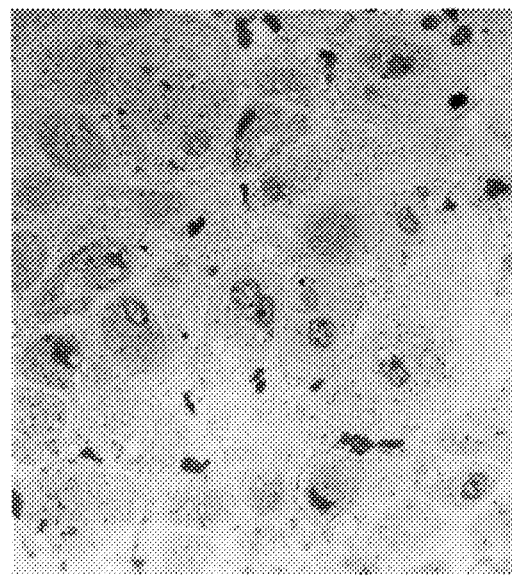

The results of decidual staining are seen in FIG. 10. FIG. 10A shows the prominent cytoplasmic staining with the anti-Hpr antibody, while FIG. 10B shows a control where the primary antibody was omitted. This experiment suggests that decidua synthesizes a protein cross-reactive with the hpr gene product under physiologic conditions.

Example 10

This example demonstrates that a protein cross-reactive with the hpr gene product expressed by decidua is synthesized as a larger polypeptide than Hpr protein isolated from pregnancy serum.

Figure 11:
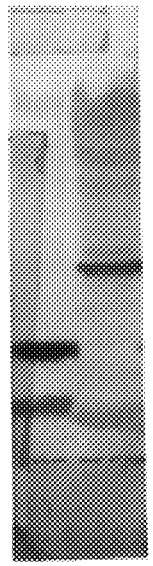
FIG. 11 depicts a Western blot analysis of reactive proteins in human decidua using polyclonal antibodies raised against the synthetic peptide made according to the predicted sequence from the hpr gene.

FIG. 11 shows that anti-Hpr recognizes an unexpectedly heavy alpha chain in lysates of decidua. Briefly, 1 g of frozen decidua was homogenized in 10 ml of lysis buffer (10 mM Tris HCl, pH 7.5 at 4', 1 mM EDTA, 1% TRITON X-100 (a polyoxyethylene ether non-ionic surfactant) 0.5 mM diisopropylfluorophosphate) using a Brinkmann polytron. Insoluble material was removed by centrifugation at 1200× g for 5 min at 4° C., and the resultant supernate mixed with Laemmli solubilizing buffer. A 50 ul aliquot was electrophoresed on a 10–15 % polyacrylamide gel, then transferred to nitrocellulose using a semi-dry blotting apparatus (Polyblot, American Bionetics). The blot was blocked for 2 h at room temperature with 3% BSA in Tris-saline, then incubated overnight in anti-Hpr, 40 ug/ml in Tris-saline. Following incubation, the blot was then sequentially washed in PBS with 0.05% TRITON X-100, incubated with biotinylated goat-anti-rabbit IgG, washed, incubated with avidin-horseradish peroxidase complex, washed, and incubated in aminoethylcarbazole substrate solution.

The blot shows that decidual lysate contains a unique alpha chain species. The left-hand lane shows a partially-purified preparation which is contaminated with haptoglobin 2; the anti-Hpr used in this experiment cross-reacts with haptoglobin 2 alpha chain, the uppermost band, but fails to react with haptoglobin 1 alpha chain. The lower band in the left-hand lane represents Hpr alpha chain from a protein cross-reactive with the hpr gene product. The right-hand lane shows that the decidual lysate contains a prominent immunoreactive band in the approximately 30 kDa range.

In liver, haptoglobins are synthesized as a single, contiguous polypeptide chain which is proteolytically cleaved to form the alpha and beta chains. Reaction of the blot with a polyvalent anti-haptoglobin antibody detected a single 45 kDa species. No mature alpha or beta chain was detected.

Example 11
Purification of OA-519 Protein from Cell Lysates.

Figure 12A:
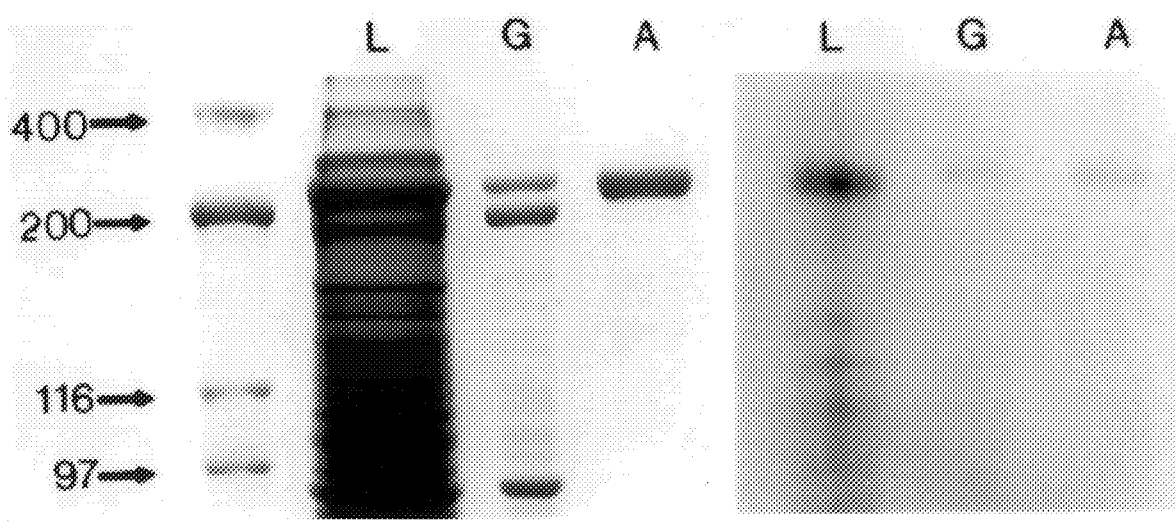
FIG. 12a depicts progressive purification of OA-519 from breast carcinoma. Polyacrylamide gel electrophoresis and corresponding Western blots are shown of sequential chromatographic purification of cytoplasmic proteins reactive with purified polyclonal anti-Hpr antibodies.

Purification of a protein which is cross-reactive with the hpr gene product from breast cancer cells is demonstrated in FIG. 12A. The Figure shows 4–8% gradient gel SDS PAGE of a protein preparation in various stages of purification. The right hand panel is stained with Coomassie Blue, and the left hand panel is a Western blot using anti-Hpr polyclonal affinity purified antibody.

ZR-75-1 human breast carcinoma cells were grown to near confluence in medium. Confluent monolayers were rinsed with phosphate-buffered saline, then scraped free, harvested by centrifugation, and stored frozen.

To each aliquot of approximately $1.5 \times 10^7$ cells, 10 ml of purification buffer (20 mM Tris HCl, pH 7.5 at 4', 1 mM EDTA, 0.1 mM diisopropylfluorophosphate, 0.1 mM phenylmethylsulfonyl fluoride) was added. Cells were homogenized with 10 strokes of a Dounce homogenizer, then clarified supernate was obtained by centrifugation at 16,000× g for 30 min. at 4° C. (Lane L of FIG. 12A was loaded with clarified ZR-75-1 hypotonic lysate.)

A Sephacryl S-200 (Pharmacia) gel filtration column, 2.5×90 cm, was pre-equilibrated with purification buffer, pH=8.0, containing 1 mM b-mercaptoethanol and 100 mM KCl. ZR-75 lysate was filtered through 0.45 mM filter, then loaded onto column at 25 ml/h. Fractions were analyzed for presence of 270,000 Da polypeptide by SDS-PAGE using a 4% Coomassie-stained gel. Presence of the polypeptide may optionally be confirmed by using Western blotting with either polyclonal antibody specific for peptide according to SEQ ID NO. 1 or anti-270 kDa protein, developing the blots with $^{125}$I-protein A. (Lane G of FIG. 12A was loaded with pooled fractions from the gel filtration column.)

Positive fractions from the Sephacryl column were pooled, diluted with an equal volume of purification buffer plus 1 mM B-mercaptoethanol then loaded onto a pre-equilibrated Mono-Q HR 5/5 anion exchange HPLC column (Pharmacia). At a flow rate of 1 ml/min., the column was washed with 15 ml of purification buffer plus 1 mM B-mercaptoethanol, eluted with linear 60 ml gradient over 60 min. to a final 1M KCl concentration, then washed with 5 ml of 1M KCl-containing purification buffer plus 1 mM b-mercaptoethanol. Fractions containing the polypeptide were selected by SDS-PAGE using Coomassi-stained 4% gels. (Lane A in FIG. 12A was loaded with pooled fractions from the anion exchange column.) Fractions containing purified polypeptide, designated OA-519, were pooled and further processed according to downstream experimental needs. Characteristic yields were roughly 1 mg of OA-519 per $2 \times 10^7$ cells with purity of 98% or greater.

Example 12
Sequences of Peptide Fragments from 270 kDa Cytoplasmic Protein.

Sequences were obtained by: (1) purification of 270 kDa polypeptide according to Example 11; (2) dialysis into 100 mM ammonium bicarbonate, pH 7.8 and proteolytic cleavage by endoproteinase Glu-C (Staphylococcal V8 protease);

(3) isolation of peptides by reversed phase chromatography in a 20 mM potassium phosphate, pH 7.8, buffer system with elution by linear gradient to 60% CH₃CN/40% phosphate buffer; (4) rechromatography on reversed phase using 0.1 %. trifluoroacetic acid in water and 0.1 % trifluoroacetic acid in CH₃CN to elute peptides; (5) quantitation and estimation of purity through amino acid analysis; and (6) determination of peptide sequence through automated Edman degradation on an Applied BioSystems gas phase sequencer. Sequences from five separate peptides are provided in the following Table 1:

TABLE 1

Peptide Sequences for OA-519 Fragments

| Peptide Sequences | Peptide Identifier |
| --- | --- |
| faalqee | OA51901.SEQ, May 22, 1991 Peptide C |
| hpesptpnpteplflaqae | OA51902.SEQ PEPTIDE K |
| havvle | OA51903.SEQ, June 12, 1991 PEPTIDE F |
| raalqe | OA51904.SEQ, June 12, 1991 PEPTIDE B2 MAJOR SEQUENCE |

A final hydroxyapatite chromatography step was added to achieve more than 99% purity using a Bio-Rad MAPS Analytical HPHT Cartridge. Using a 0–600 millimolar phosphate gradient, OA-519 elutes in one peak at 200 millimolar phosphate.

Purified OA-519 was dialyzed into 50 millimolar ammonium bicarbonate, pH 8.0 and proteolytically cleaved with a 1:50 dilution of endoproteinase glutamate C (V8 protease) for 15 minutes at 37° C. The peptides were subjected to SDS-PAGE on 4% Laemmli gels and transferred to PVDF membranes (BioRad), and were sequenced directly from the PVDF membrane using automated Edman degradation on an Applied BioSystems gas phase sequencer (Matsudaira, P. T., "A Practical Guide To Protein and Peptide Purification for Micro-Sequencing", Academic Press, New York, 1989).

Limited proteolytic cleavage generated two major peptides of approximately 150 and 134 kD. The 150 kD peptide had a blocked N-terminus and thus represented the N-terminal OA-519 peptide. N-terminal sequence was obtained from the 134 kD internal peptide which demonstrated 84.6% homology with rat fatty acid synthase over 13 amino acids as seen in FIG. 12B. Thus, OA-519 has structural homology with fatty acid synthase, also an approximately 270 kD molecule.

Example 12A
OA-519 has Fatty Acid Synthase Activity

Purified OA-519 from the ZR-75-1 human breast carcinoma cell line has fatty acid synthase activity based on its ability to incorporate acetyl coenzyme A and malonyl coenzyme A into fatty acids in the presence of NADPH. This reaction is specific for fatty acid synthase. (Wakil, S. J., Biochemistry, 28:4523–4530, 1989). Fatty acid synthesis by OA-519 was demonstrated by incorporation of $^{14}C$ malonyl coenzyme A into fatty acids, subsequent esterification of the fatty acids, and analysis by reversed-phase thin layer chromatography.

Incorporation of $^{14}C$ malonyl coenzyme A into fatty acids by OA-519: OA-519 was purified as in Example 12 except that protease inhibitors were omitted as they interfere with the final step of the synthase assay. 4.2 ug of OA-519 in 20 ul of 20 millimolar Tris HCl, 270 millimolar KCl, 1 millimolar EDTA, 1 millimolar DTT, pH 7.5 at 25° C. was added to the following reaction mixture: 75 nanomoles NADPH; 25 nanomoles acetyl coenzyme A; 16.6 ul of 1 molar potassium phosphate, pH 6.6 at 25° C.; and 97 ul HPLC grade water to a total volume of 150 ul. The reaction mixture was vortexed and 5 ul of $^{14}C$ malonyl coenzyme A (20 uCi/ml; 51 mCi/millimolar) and 25 nanomoles malonyl coenzyme A were added. Following vortexing, the reaction mixture was incubated at 37° C. for 20 minutes and stopped by the addition of 1 ml of 1:1 chloroform: methanol.

Methyl esterification of $^{14}C$ fatty acids: Prior to thin layer chromatographic separation of the $^{14}C$ fatty acid mixture, methyl esters of the $^{14}C$ fatty acids were prepared using the method of methanolic sulphuric acid. The chloroform:methanol:reaction mixture was vortexed then agitated for 30 minutes. Following centrifugation, the supernatant was dried under $N_2$. The dried lipids were extracted twice in 400 ul of hydrated n-butanol:HPLC water (1:1) pooled, washed, and dried under $N_2$. To synthesize the methyl esters, 0.75 ml of 2% sulfuric acid in methanol was added to the dried fatty acids, gassed with $N_2$, and incubated for 2 h at 70° C. Following the addition of 0.75 ml of HPLC grade water, $^{14}C$ fatty acid methyl esters were extracted twice with 1.5 ml of pentane, washed with 0.5 ml HPLC water and dried.

$^{14}C$ fatty acid methyl esters were separated and identified using reversed phase thin layer chromatography as follows. Reversed-phase thin layer chromatographic plates (20×20 cm, Analtech) were baked in a vacuum oven at 80° C. for 20 minutes. Dried $^{14}C$ fatty acid methyl esters and standards were resuspended in 20 ul chloroform:methanol (9:1), spotted, and chromatographed in chloroform: methanol:water (5:15:3). Non-radioactive standards were visualized with cyclodextrin spray in iodine vapor. $^{14}C$ fatty acid methyl esters were detected using a Bioscan System 2000 imaging scanner with Autochanger 3000.

Figure 12C:
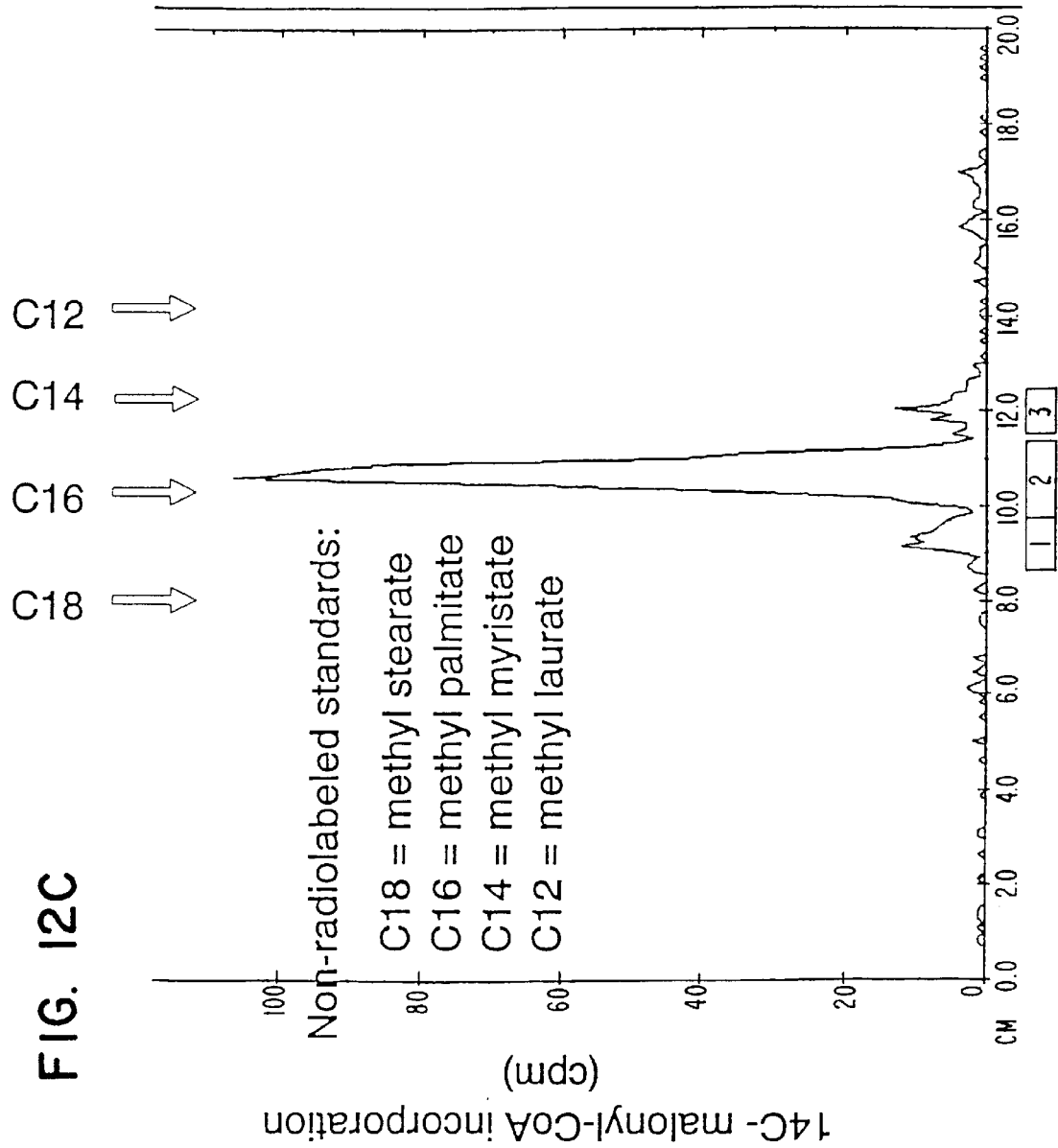
FIG. 12C shows that OA-519 synthesizes fatty acids from acetyl- and malonyl-CoA.

Results: OA-519 synthesized 85% palmitate (16 carbon saturated fatty acid), with approximately 6% myristate and 8% stearate (14 and 18 carbon saturated fatty acids, respectively) (FIG. 12C). These data demonstrate that OA-519 has fatty acid synthase activity by showing generation of complete fatty acids from $^{14}C$-labeled malonyl-CoA. The ratios among product fatty acids is similar to fatty acid synthase from human liver, but markedly different than that for fatty acid synthase from lactating human breast (34% stearate, 33% palmitate, 16% myristate).

Kinetic Characterization of OA-519 Fatty Acid Synthase

The specific activity of purified OA-519 was determined spectrophotometrically by following the oxidation of NADPH at 340 nm in the presence of acetyl coenzyme A and malonyl coenzyme A. OA-519 has a specific activity of 586 nanomoles NADPH oxidized/min/mg protein which compares favorably with the value of 404 obtained for human liver.

Spectrophotometric studies with OA-519$^{FAS}$ demonstrated that the apparent $K_m$ of $86.2 \times 10^{-5} M$ for malonyl-CoA was higher than the literature values reported for rat or rabbit mammary gland ($1.3 \times 10^{-5} M$ or $2.9 \times 10^{-5} M$, respectively) (Smith, et al., Methods Enzymol, 35:65–74, 1975; Dils, et al., Methods Enymol., 35:74–83, 1975) or for the synthase from the human breast cancer cell line SKBR3 ($1.8 \times 10^{-5}$ M) (Thompson, et al., Biochim. Biophys. Acta, 662:125–130, 1981). The $K_m$ for the purified synthase from normal human tissues has not been reported. In contrast to the $K_m$ values, the specific activity of 624 nmol NADPH oxidized/min/mg protein was similar to the reported specific activities of fatty acid synthases purified from a variety of sources including human liver (Roncari, Methods Enymol, 71:73–39, 1981).

Example 12B
Cloning of OA-519 and Determination of the Sequence of Human Fatty Acid Synthase.

The strategy for cloning human fatty acid synthase took advantage of the high degree of conservation among previously cloned fatty acid synthases, including rat, chicken, and murine forms, to generate probes likely to hybridize with human fatty acid synthase cDNA. Sequences were aligned by the GCG PILEUP program, similar to that described by Higgins and Sharp (*CABIOS*, 5:151–153, 1989). The aligned sequences identified an oligonucleotide probe with the sequence: 5'- ggg cct gga gtc tat cat caa cat cat cca cag ctc cct ggc tga gcc tcg agt gag t -3' from a region of high homology in the c-terminal third of the aligned fatty acid synthase sequences.

Initial screening used a commercial (Stratagene) oligo-dT-primed library in lambda gt11 prepared using RNA from ZR-75-1 human breast carcinoma cells, a line which produces moderately high levels of fatty acid synthase protein. Probing this commercial (Stratagene) library with an end-labeled probe having the above oligonucleotide sequence identified a 1.6 kb clone, pFAS 1.6, which contained an open reading frame corresponding by homology to the c-terminus and 3' untranslated regions of fatty acid synthase mRNA. Analysis of the pFAS 1.6 sequence identified an oligonucleotide probe from its 5' region with the sequence: 5'- aac aac cac cct ctg ggc atg gcc atc ttc ttg aa -3'. Reprobing the ZR-75-1 library with an end-labeled probe having this second oligonucleotide sequence yielded an overlapping clone, pFAS 3.0, which by homology to known sequences encoded in its open reading frame a further portion of the fatty acid synthase molecule.

Analysis of the 5' regions of pFAS 3.0 identified a third oligonucleotide with the sequence: 5'- aga act cca tac cta gca ggc tgt c -3' which was used to construct a specifically primed cDNA library. This third oligonucleotide primed reverse transcriptase-catalyzed cDNA synthesis from poly-A RNA from SKBr3 human breast carcinoma cells, a line which synthesizes extremely high levels of fatty acid synthase. The resultant cDNA was cloned into lambda Ziplox (BRL) and screened with a 1.4 kb BamH1 restriction fragment from the 5' end of pFAS 3.0 labeled by random priming; a 2.2 kb cDNA clone, pFAS 2.2, was identified. The ends of pFAS 2.2 encoded open reading frames homologous to further 5' regions of known fatty acid synthases. Rescreening of the specifically primed library with pFAS 2.2 labeled by random priming yielded two additional clones of 3.1 and 4.6 kb, designated pFAS 3.1 and pFAS 4.6, respectively.

All clones were subcloned into pBluescript and sequenced along both strands by the $^{35}$S/dideoxynucleotide method using the USB sequenase kit. Sequences were extended by standard methods including nested deletions and use of synthetic oligonucleotide sequencing primers. Together, these overlapping clones encode the complete human fatty acid synthase coding region as well as most of the 5' and 3' untranslated regions.

Figure 12D:
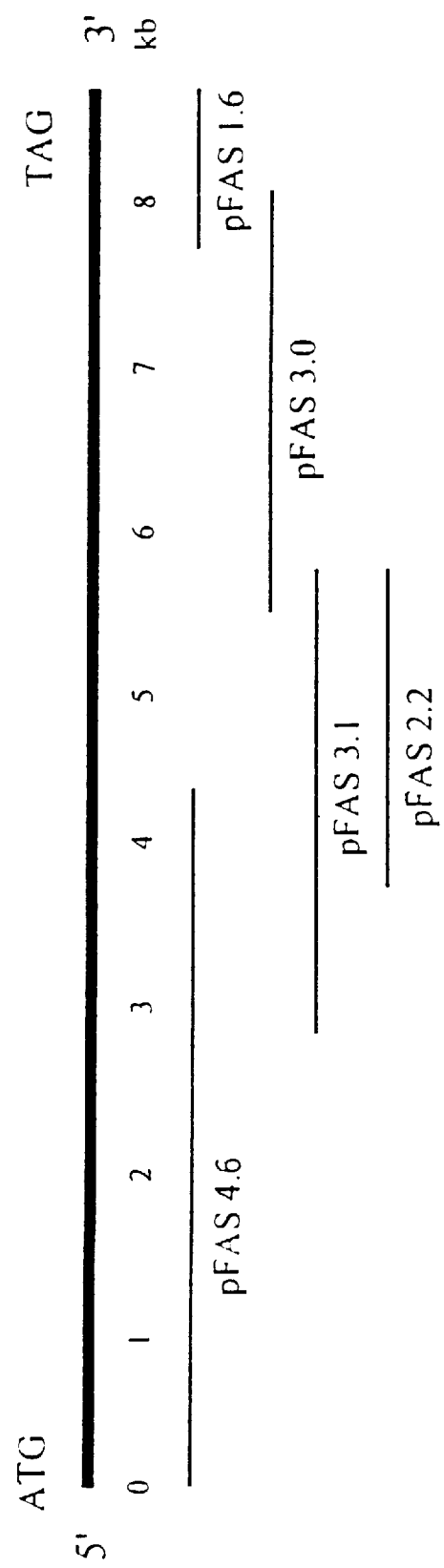
FIG. 12D shows the clone map of OA-519.

A clone map of the various clones which together encode OA-519 is shown in FIG. 12D. Cloned plasmids pFAS 1.6, pFAS 3.0, pFAS 2.2, and pFAS 4.6 were deposited with the American Type Culture Collection (ATCC), 12301 Parklawn Drive Rockville, Md. 20852, U.S.A. on Jan. 21, 1994, under ATCC Accession Nos. 75643, 75645, 75644, and 75646, respectively. A DNA molecule encoding the entire sequence of OA-519 can be assembled from these clones using standard techniques, and RNA molecules encoding all or part of the sequence prepared from expression vectors containing all or part of the DNA sequence.

Example 13
Purification of Anti-OA-519 Polyclonal Antibody
Polyclonal Antibody Production Rabbits were inoculated subcutaneously on day 0 with 200 μg of OA-519, produced as described in Example 11, in an emulsion composed of equal parts OA-519 in buffered saline and Freund's complete adjuvant. On day 14, the rabbits received booster inoculations containing the same amount of antigen in a similar mixture prepared with incomplete Freund's adjuvant. Serum was obtained on day 30 with a similar schedule maintained thereafter.

Preparation of OA-519 Affinity Column 2.5 mg of purified OA-519 at approximately 0.83 mg/ml was dialyzed into 50 mM ammonium bicarbonate, 150 mM NaCl, pH 8.5 at 4° C. The OA-519 was coupled to 2 ml of Reacti-Gel 6X (Pierce) for 45 hrs., achieving 98% coupling efficiency by BCA protein microassay (Pierce). Excess reactive sites on the Reacti-Gel were blocked by incubation with 2 ml of 100 mM Tris-HCl, pH 8.2, at 4° C., overnight.

Affinity Purification of Polyclonal OA-519 Antibody

Before running, the affinity column was cycled sequentially with 10 column volumes of phosphate buffered saline (PBS) with 1 mM sodium azide, pH 7.5, followed by the same buffer with 6M urea, and finally, PBS/1 mM sodium azide. For each run, 5 ml of serum was diluted 1:2 with PBS/1 mM sodium azide, and pumped on the column at 0.25 ml/min. The column was washed with PBS/1 mM sodium azide then eluted with PBS containing 6M urea. Eluted fractions were dialyzed exhaustively against PBS/1 mM sodium azide. Each run produces about 100–200 ug of antibody as determined by the BCA protein microassay (Pierce).

Example 14
Purified OA-519 Reacts with Anti-Peptide Antibody and Anti-OA-519.

Figure 13:
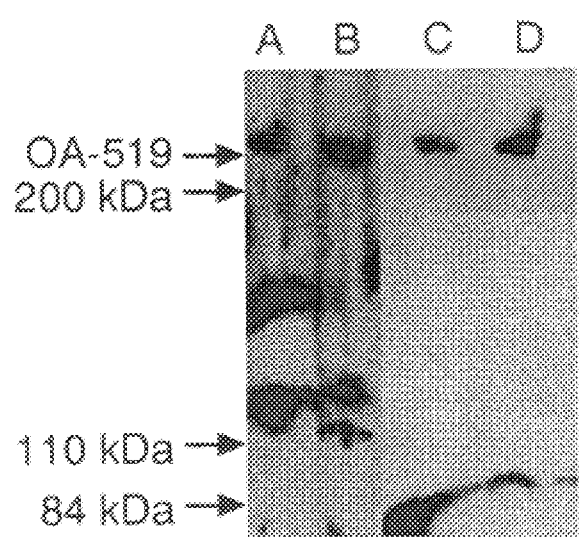
FIG. 13 depicts Western blot analysis of OA-519 using antibodies raised against the synthetic peptide (Lanes A-B) or antibodies raised against purified OA-519 (Lanes C–D).
Figure 14A:
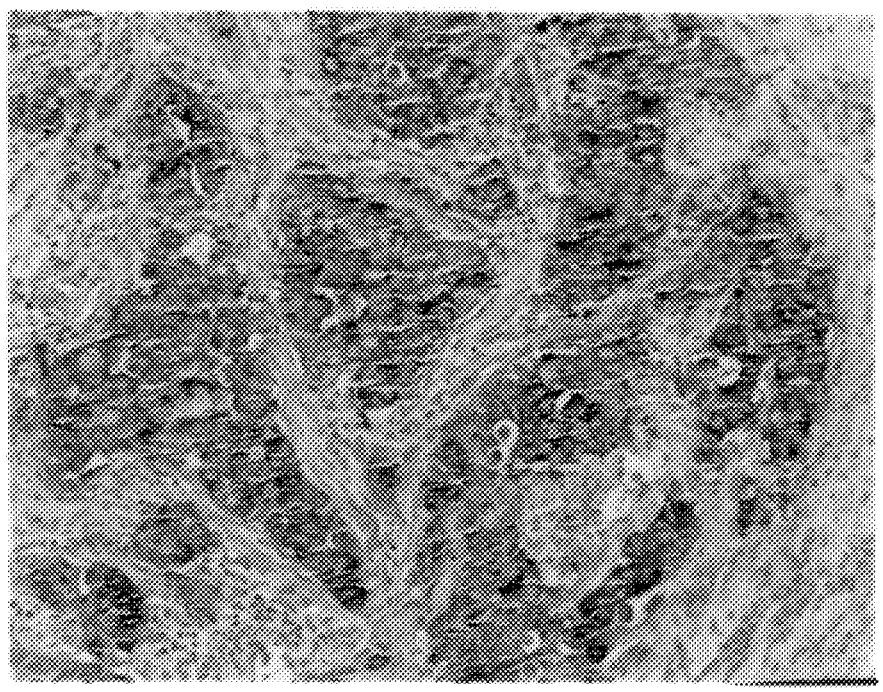
FIG. 14 shows immunohistochemical staining of human breast carcinoma using antibodies raised against purified OA-519.
Figure 14B:
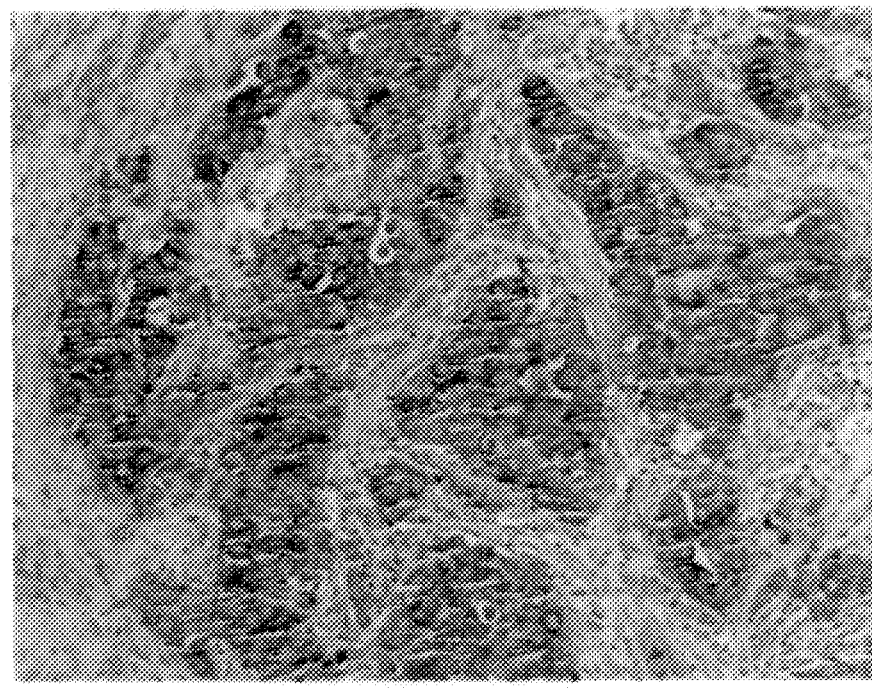

FIG. 13 represents a Western blot of a 4% Laemmli gel containing 10 ug of OA-519, purified according to Example 11, in each lane. Each lane was incubated with the indicated antibody at the specified concentration, then developed using $^{125}$I-protein A. Lane A was developed with 10 ug/ml of affinity-purified rabbit polyclonal anti-Hpr peptide antibody prepared by immunizing rabbits with a peptide according to SEQ ID NO. 1; Lane B was developed with 17 ug/ml of affinity-purified rabbit polyclonal anti-peptide antibody; Lane C was developed with 13 ug/ml of affinity-purified rabbit polyclonal anti-OA-519, according to Example 13; Lane D was developed with 20 ug/ml of affinity-purified rabbit polyclonal anti-OA-519. The dark splotches of MW below 200 kDa represent artifact.

Example 15
Identification of OA-519 in Human Breast Carcinoma Extracts.

Fresh human breast carcinoma tissue was homogenized in 20 mM Tris HCl, pH 7.5 at 4', 1 mM EDTA, 0.1 mM diisopropylfluorophosphate, 0.1 mM phenylmethylsulfonyl fluoride, then fractionated on a Sephacryl S-200 (Pharmacia) gel filtration column, 2.5×90 cm, with 20 mM Tris HCl, pH 8.0, 100 mM KCl, 1 mM b-mercaptoethanol. Fractions were analyzed by SDS-PAGE for the presence of 270 kDa species. Fractions were normalized to contain amounts of the 270 kDa species equivalent to that in a preparation of purified OA-519 according to Example 11. The normalized fractions were electrophoresed on a 4% Lammeli gel side by side with purified OA-519 and analyzed by Western blotting using either affinity-purified rabbit polyclonal anti-Hpr antibody (according to Example 6), or affinity-purified rabbit polyclonal anti-OA-519 (according to Example 13). The blot was developed with $^{125}$I-protein A. The developed blot showed that anti-Hpr peptide antibodies and anti-OA-519 antibodies both detect the equivalent 270 kDa species in an OA-519 preparation purified from a breast cancer cell line and in an extract of breast carcinoma tissue.

Example 16
Monoclonal Antibodies Against OA-519.

Monoclonal antibodies were prepared according to a modification of the method described by Zola (Monoclonal Antibodies, a Manual of Techniques, Boca Raton, Fla., CRC Press, 1987, pp. 29–75). These BALB/c mice were immunized using an Hpr-derived synthetic peptide-keyhole-limpet hemocyanin conjugate (Kuhajda, et al., *Proc. Natl Acad. Sci. U.S.A.*, 1989, 86:1188–92; Kuhajda, et al., *N. Engl. J. Med.*, 1989, 321:63641), and their spleens fused with the SP2 murine myeloma cell line. Only antibodies that reacted with tumor sections known to be positive with the polyclonal antibody were finally selected. The monoclonal antibody was purified from ascites by protein A-Sepharose affinity chromatography with elution by 6M urea in phosphate buffered saline (PBS). The eluate was collected and dialyzed against PBS overnight in the cold, aliquoted and stored frozen at −80° C. or lyophilized.

Hybridoma cells from this fusion, designated OA-519-M1 or HPR-2, were deposited with the American Type Culture Collection, 12301 Parklawn Drive, Rockville, Md. 20852, on Jul. 26, 1991, as ATCC Accession No. 10853.

Example 17
Staining Paraffin Tissue Sections.
Antibody Solution

Monoclonal antibodies according to Example 16 were recovered from hybridoma supernate, purified by Protein A affinity chromatography and lyophilized. Deionized water was added to lyophilized antibody, to prepare 0.125 mg/ml stock antibody solution. The stock antibody should be kept frozen in aliquots at −70° C. Bovine serum albumin was not added to solutions. An appropriate volume of stock antibody was diluted $\frac{1}{25}$ with a rinse buffer, pH=7.5, (preferably 1× Automation buffer, Biomeda #M30 buffer) for a working solution.
Tissue Slide Preparation Tissue sections were deparaffinized and hydrated to water, and endogenous peroxidase activity was blocked with 3% $NH_2O_2$ in methanol for 20 minutes. Then the slide was rinsed 5 minutes in rinse buffer and incubated in 10% normal rabbit serum in rinse buffer for 30 minutes at room temperature.
Reaction with Monoclonal Antibody and Stain Excess rabbit serum solution was removed, and working antibody (diluted $\frac{1}{25}$ in rinse buffer) was added. The slide was incubated for 1 hour at 37° C., then drained and rinsed in rinse buffer. The slide was incubated in $\frac{1}{200}$ biotinylated rabbit anti-mouse antibody (DAKO E-354) for 1 hour at 37° C. and rinsed in rinse buffer. Then the slide was incubated with avidin-linked horse radish peroxidase (Vectastain Elite Standard #PK6100) for 1 hour at 37° C. and rinsed in rinse buffer for 1 hour at 37° C. After the avidin-biotin complex formation, the slide was incubated in amino ethyl carbazole for 7 min. (Biomeda #501) and rinsed with deionized water. Counter stain was applied (Biomeda's M-10 Aqueous Hematoxylin) and a coverslip, and the slide was observed by light microscopy.
Staining Pattern Observed by Light Microscopy.

The following is a general description of the staining patterns observed for patients whose tumor was positive for the presence of OA-519. Tumor staining was visible at the "low power objective", i.e., 100–150×. This method is roughly equivalent to reactivity in 10% or greater of the tumor cells. Patients whose breast cancers have reactivity identified only at higher magnifications or in less than 10% of the cells are not considered positive.

The pattern for positive staining was strictly cytoplasmic and often had a distinctive granular appearance. While light diffuse cytoplasmic reactivity occurred occasionally, a granular staining pattern was often visible in the setting of diffuse staining. Positive staining occasionally occurred without clear granularity. Nuclear reactivity has not been observed; if found it is indicative of artifact and must not be interpreted as a positive result.

Staining is preferably assessed in infiltrating carcinoma. Reactivity usually varies from cell-to-cell and region-to-region of the tumor, reflecting heterogeneity. If all of the cells in a tumor show identical levels of reactivity, the result is probably not positive. When this type of diffuse staining occurs, granular staining will often not be identified and the case should not be considered positive. Some diffuse background reactivity has been noted in smooth muscle of the nipple, in some blood vessels, and in dense collagen. This nonspecific staining should not be confused with reactivity in breast carcinoma.
Anti-OA-519 Reactivity in Human Breast Carcinoma.

Figure 16A:
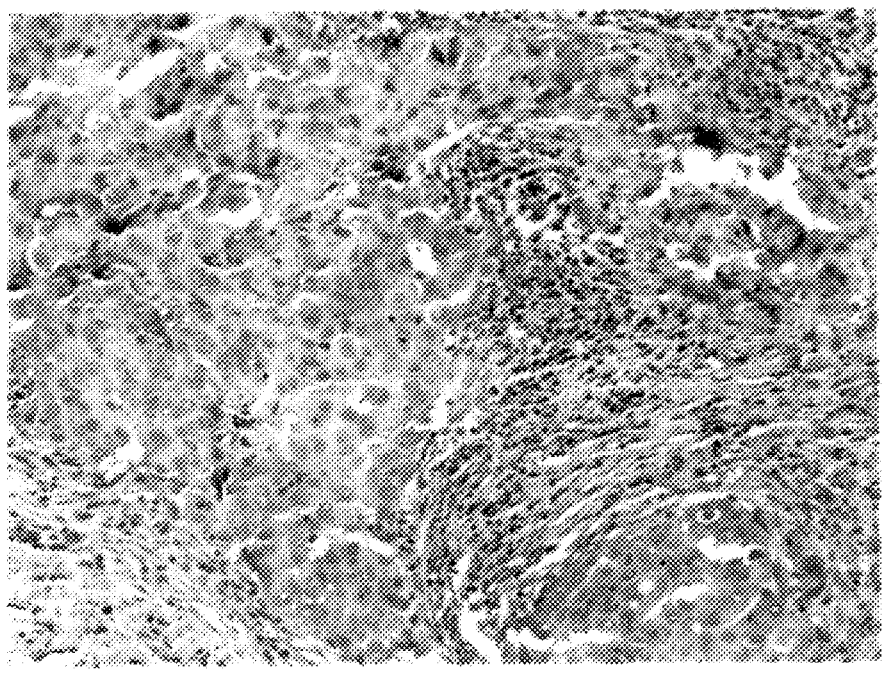
FIG. 16 shows the same experiment as FIG. 15 except the antibodies were pre-incubated with purified OA-519.
Figure 16B:
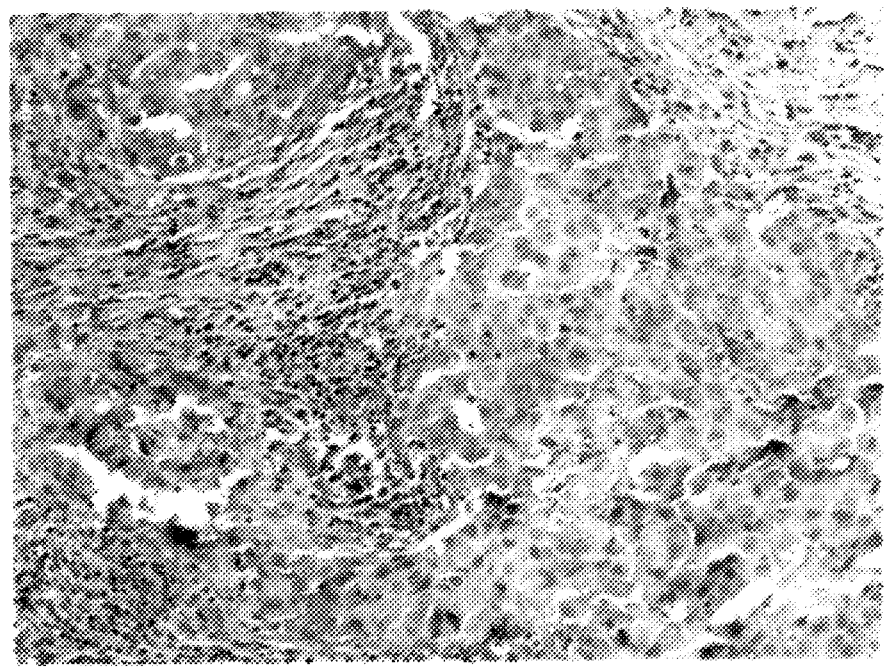
Figure 17A:
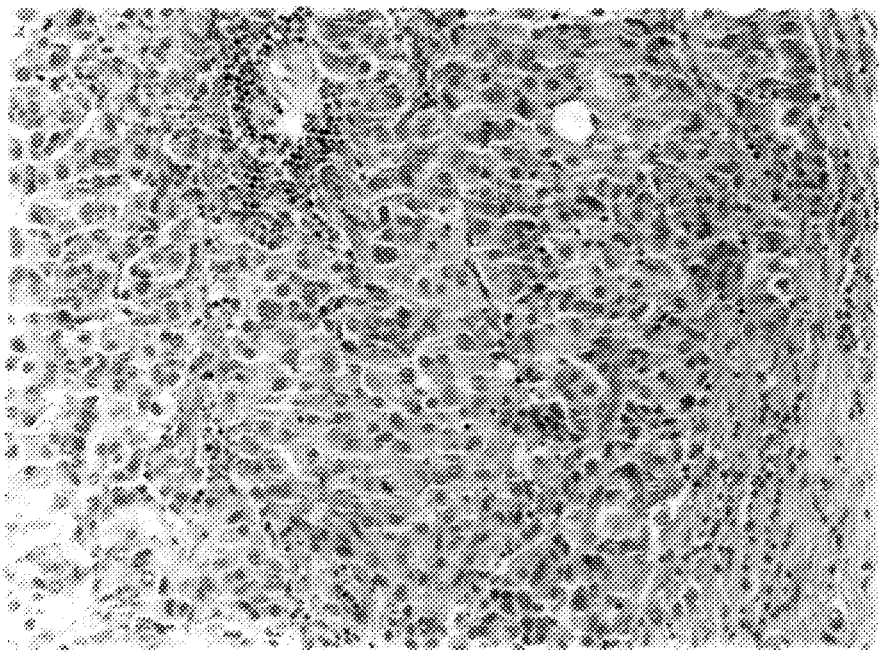
FIG. 17 is a control slide of breast carcinoma in which the primary antibody was omitted from the staining protocol.
Figure 17B:
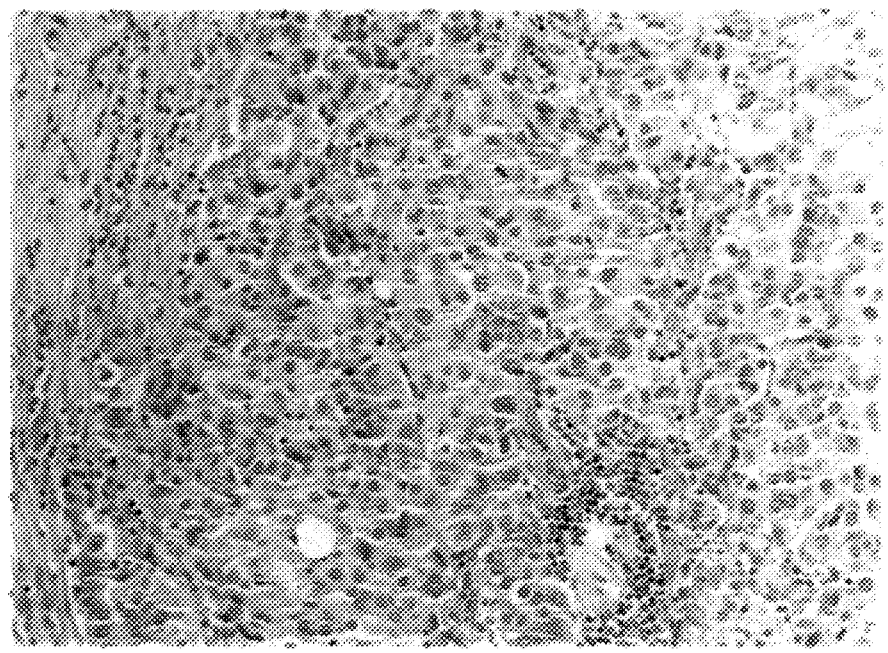

FIGS. 14–17 show histologic sections of human breast carcinoma immunohistochemically stained as described in Example 17 with various antibodies: affinity-purified rabbit polyclonal anti-OA-519 antibody according to Example 13 (FIG. 14), affinity-purified rabbit polyclonal anti-Hpr peptide antibody according to Example 6 pre-incubated with bovine serum albumin (FIG. 15), affinity-purified rabbit polyclonal anti-Hpr peptide antibody pre-incubated with a 33-fold molar excess of OA-519 (FIG. 16), and a control slide omitting primary antibody (FIG. 17). The dark cytoplasmic staining represents immunohistochemical detection of OA-519, shown in both FIG. 14 and FIG. 15. FIG. 16 shows that pre-incubation with OA-519 ablates staining with the anti-Hpr peptide antibody, indicating the presence of a shared epitope. Pre-incubation of the anti-Hpr peptide antibody with unrelated protein (bovine serum albumin) had no effect (FIG. 15).

Example 18
OA-519 Expression is Associated with Decreased Survival in Breast Carcinoma.

Breast Cancer Patient Population: An inception cohort (patients entered into the study at the time of initial surgical treatment) of one hundred and thirty-five women with breast cancer were identified by the Norton Hospital tumor registry, all of whom were treated with mastectomy for primary infiltrating ductal breast carcinoma. The average patient age was 52 and ranged from 32 to 72 years. The average follow-up was 12.3 years and ranged from 10 to 16 years. Patients were admitted to the study when post-surgical treatment records, cause of death, survival time, and paraffin blocks of primary tumor were available for each patient. Estrogen and progesterone receptor information was determined immunohistochemically. In addition, patient age, dose and type of chemotherapy, radiotherapy, and hormonal therapy were documented. Type of infiltrating tumor and nuclear grade were also assessed using the criteria of Fisher et al (Fisher, et al, *Cancer,* 46:908–918, 1980).

Immunohistochemical Staining for OA-519: Immunohistochemical staining used monoclonal anti-OA-519 antibodies from hybridoma cells designated OA-519-M1 or HPR-2, which were deposited with the American Type Culture Collection, 12301 Parklawn Drive, Rockville, Md. 20852, on Jul. 26, 1991, under ATCC Accession No. HB 10853. Subsequently, additional slides from the same patients were stained with affinity-purified polyclonal antibodies prepared by immunizing rabbits with OA-519, yielding substantially equivalent results.

Briefly, the primary anti-OA-519 monoclonal antibody was incubated on the deparaffinized tissue sections at 2.5 ug/ml for 1 hour at 37° C. Following rinsing in rinse buffer, the slides were then incubated in 1/400 rabbit anti-mouse antibody (DAKO) for 1 hour. Following another rinse, the slides were incubated with avidin-linked horseradish peroxidase (Vectastain® ABC kit) for 1 hour. After the avidin-biotin complex formation, the slides were incubated in aqueous hematoxylin, coverslipped and observed.

OA-519 Immunoreactivity and Criteria for Positivity: Positive staining was finely granular, cytoplasmic, and heterogeneous. Additionally, staining either had to be visible at 100× magnification, or label at least 10% of tumor cells for a case to be scored positive.

Figure 18:
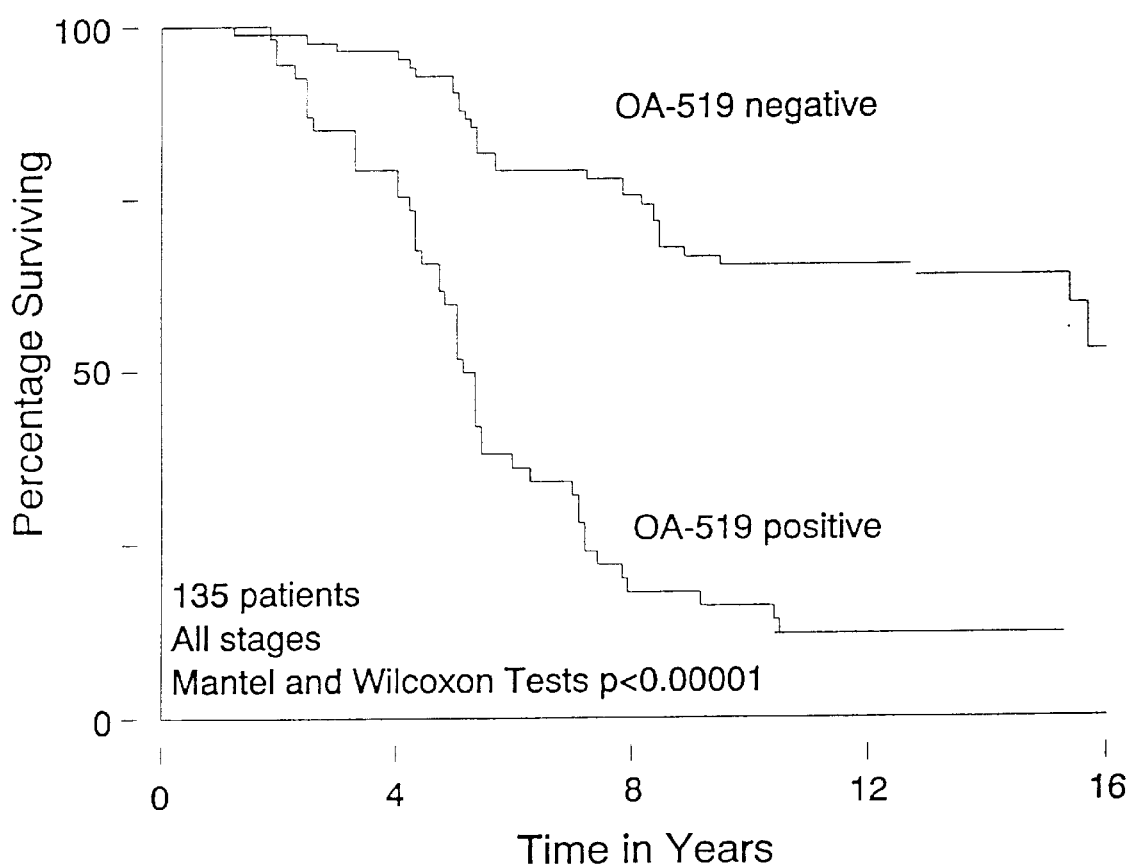
FIG. 18 shows the correlation between OA-519 expression and survival in breast carcinoma.

Prognostic Significance of OA-519 Immunoreactivity: Patients whose tumor-stained positively for OA-519 had a markedly increased risk of dying of breast carcinoma. FIG. 18 is a life table which shows the fate of OA-519 positive and negative patients. For example, after 12 years, about 37% of the OA-519 negative patients were dead compared to approximately 85% of the OA-519 positive patients.

The following table shows the significance of OA-519 reactivity by stage:

|  | STAGE 1 % dead | STAGE 2 % dead | STAGE 3 % dead |
| --- | --- | --- | --- |
| OA-519+ | 9/13 (70%) | 27/31 (87%) | 9/9 (100%) |
| OA-519− | 3/20 (15%) | 16/41 (39%) | 12/21 (57%) |
| p-value | 0.002 | <0.0001 | 0.019 |

Comparison with Other Prognostic Markers

OA-519 expression was strongly prognostic in early breast cancer, as shown in Example 1. This prognostic potential was independent of the prognostic power of estrogen and progesterone receptors. Increased expression of OA-519 in human breast carcinoma conferred a significantly worsened prognosis as measured either by disease recurrence or overall survival. In a clinical study of 135 patients with Stage I–III breast carcinoma (Martin, et al., manuscript in preparation), Cox multi-variate proportional hazard analysis demonstrated that OA-519 and progesterone receptor expression were most strongly and independently associated with adverse survival regardless of stage (univariate relative risk 4.860, 0.070; multi-variate relative risk 2.567, 0.153, respectively).

Figure 19:
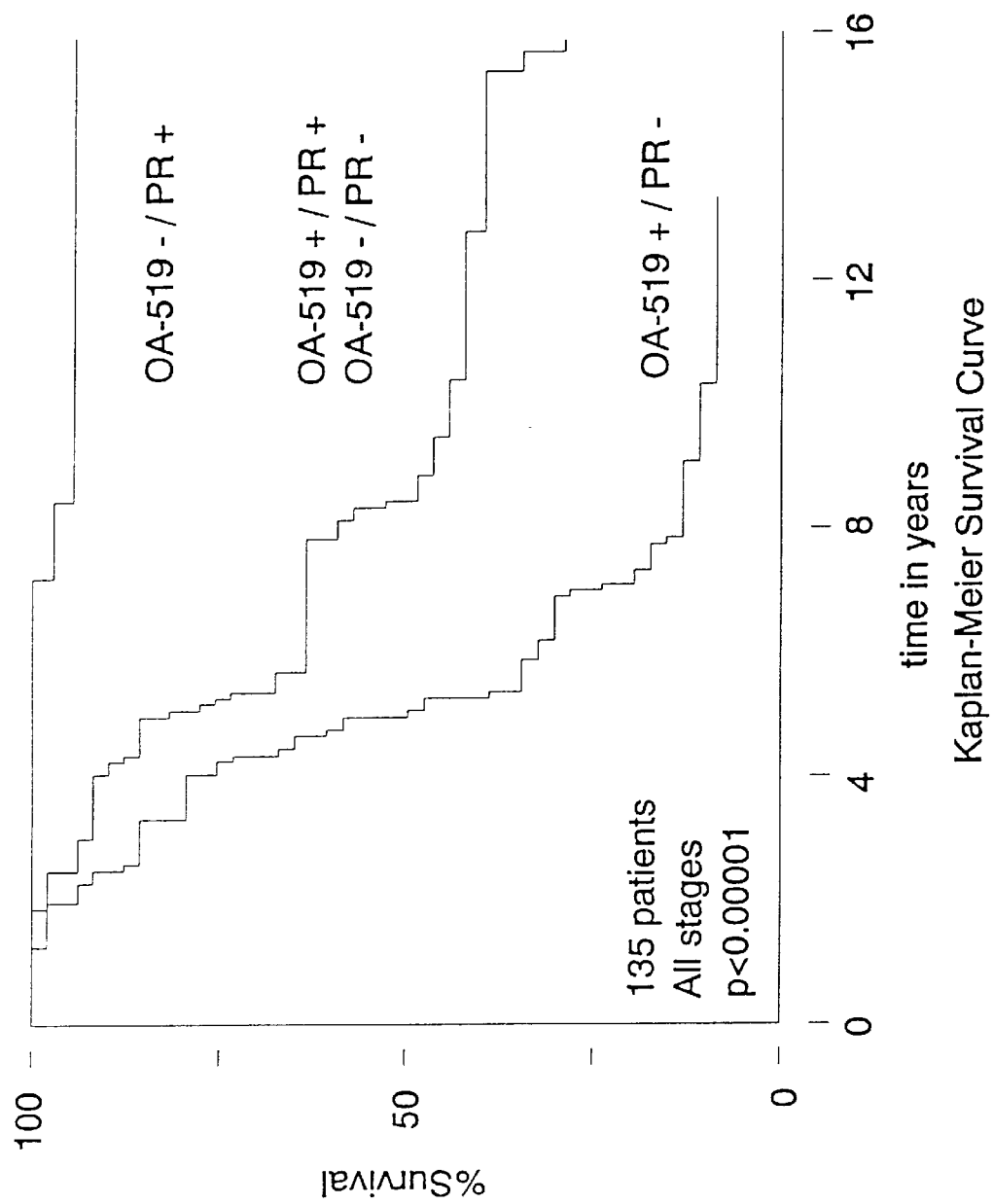
FIG. 19 shows the prognostic correlation between expression of OA-519 and progesterone receptor (PR) in breast cancer.

The prognostic power of OA-519 expression is further illustrated by the accompanying Kaplan-Meier plots (FIGS. 18 and 19). FIG. 18 demonstrates that about 10% of OA-519 positive patients survived for 15 years as compared to about 50% of OA-519 negative patients. FIG. 19 graphically demonstrates the improved prognostic stratification when the two independent prognostic markers, OA-519 and progesterone receptor, are combined. This allowed stratification of patients into an OA-519 positive, progesterone receptor negative high risk group (88% dead), an OA-519 negative/progesterone receptor positive low risk group (5.4% dead), and an intermediate risk group (63% dead).

Among other markers included in this study, OA-519 was independent of p185$^{neu}$ and cathepsin D expression. Interestingly, OA-519 expression was not associated with tumor cell proliferation as measured by proliferating cell nuclear antigen. In a separate study of OA-519 expression and S-phase determined by flow cytometry, OA-519 expression also showed no association with the S-phase fraction (Shurbaji, et al., Lab Invest., 68:69A, 1993). Therefore, OA-519 expression could be utilized with the aforementioned, or any other independent prognostic marker to improve stratification of the patient population.

Example 19A

Expression of Hpr-epitopes by Prostatic Adenocarcinoma.

Forty-two consecutive cases of prostate adenocarcinoma were selected from the files of the Mountain Home VA Medical Center. The specimens consisted of 23 transurethral resections (TUR), 14 needle biopsies, and five prostatectomy specimens.

Clinical Stage information was obtained from the tumor registry abstracts or by review of the clinical records.

Histopathologic Studies

Tumor grading: All slides were reviewed and a Gleason score was determined by adding the numbers for the two most predominant patterns (Gleason, in Tannenbaum M (ed): Urologic pathology: The prostate. Philadelphia, 1988, Lea & Febiger, pp. 171–198.). Gleason scores 2–4 were assigned Grade I, scores 5–7 were assigned grade II, and scores 8–10 were assigned Grade III.

Tumor volume estimation in TUR specimens: The method of Humphrey and Vollmer (Hum. Pathol., 19:411–418, 1988) was used, and the ratio of "chips" with cancer to the total number of chips was determined, expressed as a percentage and used as a measure of tumor volume in TUR specimens.

Immunohistochemical Studies

A single representative tissue block was selected from each cancer for immunohistochemical staining.

An affinity purified polyclonal anti-Hpr peptide antibody was used in this study. This antibody was raised against a synthetic peptide corresponding to the 34N-terminal residues of the predicted gene product (see Example 6). Staining was performed on routinely processed, formalin fixed, paraffin embedded tissue. The Avidin-Biotin Complex (ABC) immunoperoxidase technique utilizing unlabeled primary antibody was used. In brief, 6 mm deparaffinized and rehydrated tissue sections were incubated in 3% hydrogen peroxide in methanol for 15 minutes to block endogenous peroxidase activity, and then in a 1:20 dilution of normal goat serum in phosphate-buffered saline (PBS) for 30 minutes. Slides were then incubated with affinity-purified polyclonal anti-Hpr peptide at 5 ug/ml in 1% bovine serum albumin (BSA) in PBS at pH 7.2 for one hour at room temperature. Alternatively, an overnight incubation at 4° C. can be used with comparable results. With intervening washes with PBS, the sections were successively incubated with biotinylated goat anti-rabbit immunoglobulin diluted 1:500 in 1% BSA in PBS (Vector Laboratories) and avidin-horseradish peroxidase complex (Vectastain®, Vector Laboratories), both for 30 minutes at 22° C. Aminoethyl-carbazole (AEC) (Vector Laboratories) was used as the chromogen with Mayer's hematoxylin counterstain. For negative controls, PBS was substituted for primary antibody for each case. A known anti-Hpr positive case was used as a positive control with every run.

Staining was defined as positive for Hpr epitopes if (1) immunoreactivity was discernible at lower power (100×) (2) granular cytoplasmic staining was present without observable nuclear staining, and (3) staining was heterogeneous (i.e., the level of reactivity varied from cell to cell or from region to region. Tumors were scored as positive or negative.

Hpr Epitope Expression and Tumor Grade

Twenty (48%) of the 42 prostate cancers were positive for Hpr epitopes, while 22 (52%) were negative. No staining was noted in normal or hyperplastic prostate tissue. Hpr epitope expression occurred in 6 (67%) of nine Grade III, 14 (61%) of 23 Grade II, and in none (0%) of ten Grade I cases. The differences in the proportion of the positive staining cases was highly statistically significant when Grade I was compared to Grade II or Grade III (Fisher exact probability: $p<0.002$, $p<0.006$, $p<0.0009$, respectively). The difference in the proportion of positive staining cases between Grades II and III was not statistical significant.

Hpr Epitope Expression And Tumor Volume

Twenty-three TUR specimens were included in this study. Of these, eleven (48%) stained positive for Hpr epitopes, while 12 (52%) were negative. The similarity of the proportion of positive cases to that of the entire group was striking, and provided further assurance that this is representative group. Tumor volume was estimated in all of these TUR specimens by the ratio of chips with cancer to the total number of chips examined (Humphrey and Vollmer). The mean percent of "chips" with tumor in the positive group was 57% (range:2–100), while that in the negative group was 15% (range: 1–75%). The difference between the two means was highly statistically significant ($t=2.9$, $p=0.004$).

Hpr Epitope Expression and Clinical Stage

The specimens examined in this study consisted of 12 Stage A, 13 Stage B, five Stage C, and 12 Stage D cancers. A clear trend towards a higher proportion of positive cases with advancing clinical stage was observed. Only 25% of Stage A cases expressed Hpr epitopes with 46%, 60% and 67% for Stages B, C, and D, respectively. These differences were not, however, statistically significant.

Hpr epitopes are expressed by some prostate cancers, and expression of these epitopes is not seen in normal or benign hyperplastic prostate tissues. There is a statistically significant correlation between Hpr-epitope expression and higher tumor grades and larger tumors. In addition, the proportion of tumors expressing Hpr-epitopes tends to increase with advancing clinical stage. Since high tumor grades, large tumor volumes, and advanced stage are proven indicators of poor prognosis, Hpr-expression is potentially of prognostic significance in prostate cancer.

Example 19B. Expression of OA-519 by Prostatic Adenocarcinoma

OA-519 expression in prostate cancer was also found to be associated with disease recurrence. Patients having been diagnosed and treated for prostate adenocarcinoma were selected from the files of the Mountain Home VA Medical Center. The study population included 99 patients with prostate cancer in American Urologic System (AUS) stages A through D1. Clinical Stage information was obtained from the tumor registry abstracts or by review of the clinical records. Patients were excluded from the study is they had distant metastasis at the time of presentation (AUS stage D2), their status at last follow up was unknown, or if the total follow up was less than two years.

Immunohistochemical Studies

A single representative tissue block was selected from each cancer for immunohistochemical staining. An affinity purified polyclonal antibody raised in rabbits against purified OA-519 was used in this study. Staining was performed on routinely processed, formalin fixed, paraffin embedded tissue. The Avidin-Biotin Complex (ABC) immunoperoxidase technique utilizing unlabeled primary antibody was used. In brief, 6 mm deparaffinized and rehydrated tissue sections were incubated in 5% nonfat dry milk in phosphate buffered saline (PBS) including 3% hydrogen peroxide for 20 minutes to block endogenous peroxidase activity as well as non-specific protein interactions. Slides were then incubated with affinity-purified polyclonal anti-OA-519 at 2.7 ug/ml in PBS at pH 7.2 for one hour at room temperature. With intervening washes with PBS, the sections were successively incubated with biotinylated goat anti-rabbit immunoglobulin diluted 1:200 in PBS (Vector Laboratories) and avidin-horseradish peroxidase complex (Vectastain®, Vector Laboratories), both for 30 minutes at 22° C. Aminoethylcarbazole (AEC) (Vector Laboratories) was used as the chromogen with Mayer's hematoxylin counterstain. For negative controls, PBS was substituted for primary antibody for each case. A known anti-OA-519 positive case was used as a positive control with every run.

Staining was defined as positive for OA-519 epitopes if (1) immunoreactivity was discernible at lower power (100×) (2) granular cytoplasmic staining was present without observable nuclear staining, and (3) staining was heterogeneous (i.e., the level of reactivity varied from cell to cell or from region to region. Tumors were scored as positive or negative. Positive staining for OA-519 was seen in 56 (57%) of the 99 primary prostate cancers examined.

The mean total follow up time was 4.17 years (range, 2.01–9.33). Prostate cancer recurred or progressed in 19 (19%) of the patients. Progression was defined as the appearance of local or metastatic disease after "curative" treatment, such as radical prostatectomy or radiation, or advance in the stage of disease in patients treated with hormonal therapy or expectantly managed. The average time to progression of disease was 2.54 years (range 0.67–5.85).

Figure 20:
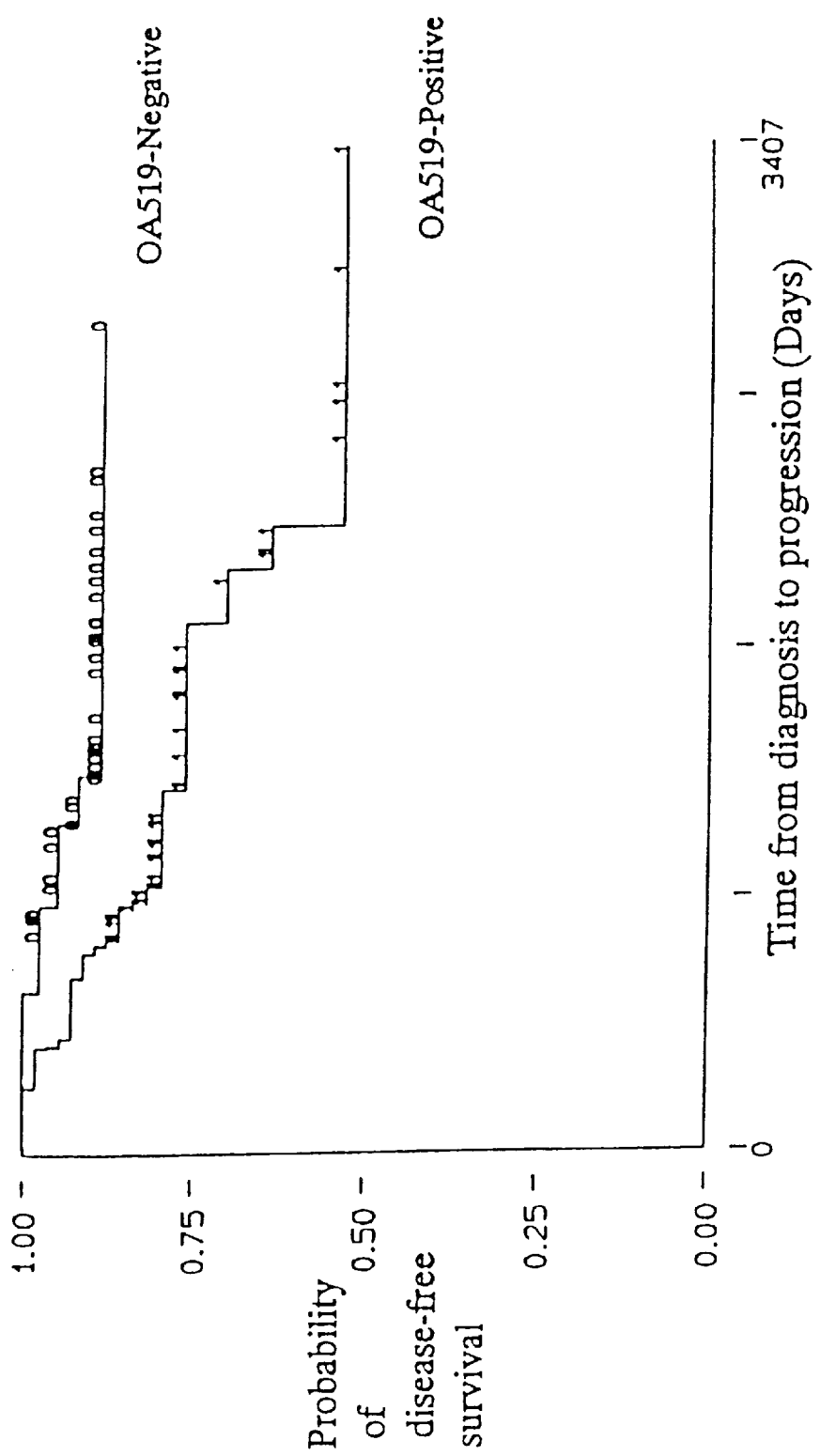
FIG. 20 shows the correlation between OA-519 expression and disease free survival in prostate cancer.

There were four (9%) cases of disease progression among the OA-519-negative group compared to 15 (27%) in the OA-519-positive group (Kaplan-Meier plot shown in FIG. 20). The difference between these groups in the proportion of cancers that progressed was statistically significant (Wilcoxon and log rank tests ($P<0.009$) and Fisher exact test ($P<0.04$)). OA-519 was a particularly valuable prognostic indicator among the low and intermediate grade prostate cancers, where the histologic grade by Gleason score was not a significant prognostic indicator (data not shown).

Example 20

Tissue Stains of Various Carcinomas

The following carcinomas have been tested for immunoreactivity using the polyclonal affinity purified anti-Hpr antibody:

breast colon lung (non-small cell)

prostate ovary endometrium stomach pancreas esophagus (squamous carcinoma)

larynx (squamous carcinoma)

renal cell carcinoma (kidney)

All of these tumors show cytoplasmic reactivity with anti-Hpr antibody. Colon, lung, prostate, ovary, stomach, and kidney have all shown differential staining (some tumors have positive staining and samples from other tumors are negative).

Ovarian Carcinoma

An ovarian carcinoma study by Kacinski et al. is in progress using the same antibody, staining procedure, and interpretation that was used in the above breast carcinoma study. However, based on analysis of 34 patients completed so far, there is an association of OA-519 expression with reduced disease-free and overall survival, which is demonstrated in FIG. 21.

Example 21

Serum Assay for OA-519.

OA-519 can also be detected in the serum of a patient having a tumor which expresses the antigen. A serum sample is obtained from a patient suspected of having a metastatic tumor and clarified by centrifugation. A high molecular weight fraction of the serum sample is electrophoresed on a 4% Lammeli gel and analyzed by Western blotting using purified polyclonal anti-OA-519 antibody according to Example 13. The blot is developed with $^{125}$I-protein A. A band at the level of 270 kDa in the Western blot indicates the presence of OA-519.

Example 22

Enzyme Linked Immunosorbent Assay (ELISA) To Circulating OA519™

Monoclonal antibodies reactive with OA519™ were produced by immunizing female Balb/C mice with purified OA519, isolating antibody producing B-cells from the spleen and fusing them to F/0 mouse myeloma cells using polyethylene glycol. Hybridomas which produced antibodies reactive with OA519 were selected using a plastic microtiter plate which had OA519 adsorbed to it. Selected hybridomas were cloned by limiting dilution and subclonal three times by limiting dilution to ensure monoclonality. Monoclonal antibodies which were able to react with OA519 in blood were selected for use in the ELISA assay. Their specificity was confirmed by evaluation of purified OA519 on Wester blots and by detection of circulating OA519 in blood samples containing elevated OA519 by Western blots.

Polyclonal anti-OA519™ antibodies were generated in rabbits by immunizing them with purified OA519 in Freunds complete adjuvant followed by booster injections in Freunds incomplete adjuvant. After test bleeds showed a response, assessed by antibody binding to OA519 adsorbed to plastic microtiter plates, a volume of blood was removed. The antibodies were separated by ion exchange chromatography or affinity chromatography and conjugated with biotin for use as the secondary antibody in the ELISA format.

The assay of soluble OA519™ was performed as follows: Calibrators containing known amounts of OA519 or unknown specimens were added to microtiter plate wells which have been coated with monoclonal anti-OA519 antibodies and incubated for two hours at room temperature (15°–30° C.). The calibrator or specimen was removed and the wells were washed with a phosphate buffered saline-Tween solution. The antibody bound the OA519 present in the calibrators and specimens and retained it in the microtiter plate well. The secondary anti-OA519 (rabbit) antibody which has been biotinylated was then added to the washed wells. If OA519 was present, the secondary antibody reacted with the bound antigen and formed a "sandwich". After a two-hour, room temperature incubation, the unreacted secondary antibody was washed away as above.

To detect the presence of the biotinylated antibody, streptavidin conjugated with horseradish peroxidase (HRP) was added which binds to the biotin. After 1 hour room temperature incubation, the unreacted streptavidin-HRP was washed away. To detect the HRP bound to the rabbit anti-OA519, substrate (hydrogen peroxide and ortho-phenylene diamine) was added and allowed to react for 30 minutes at room temperature. Sulfuric acid was added to stop the enzyme reaction and fully develop the color. The intensity of the color was measured in an appropriate spectrophotometer at a wavelength of 490 nm. The intensity was directly proportional to the quantity of OA519 in the calibrator or unknown. The unknowns were quantitated by interpolation from the calibrator curve and correcting for any dilution factor used.

Calibrator curves generated by four different individuals fit a 3rd order polynomial equation, although point-to-point or other data reduction equations could be used. When each calibrator and unknown was assayed in duplicate and the absorbances averaged to generate the calibrator curve, the % C.V.'s (standard deviation divided by the mean times 100) were typically less than 10% (intra-assay). The day-to-day and person-to-person reproducibility (inter-assay) was assessed by quantitating a specimen containing OA519. This was assayed by five people on different days. The overall mean dose was 10.2 ng OA519/ml, the standard deviation was 1.2 ng OA519/ml which results in an interassay % C.V. of 12.1%

To confirm the specificity of the assay and verify the dose-response relationship, normal human serum and matched EDTA plasma samples were spiked with purified OA519. These were then serially diluted in the unspiked calibrator buffer and assayed. The dose response was linear for both serum and EDTA plasma, again supporting the specificity of the assay system.

Example 23

Diagnostic Use of ELISA assay for Circulating OA-519

ELISA determination of circulating OA-519 was performed for a number of individuals and correlated with the state of neoplastic disease in these individuals. Plasma specimens were obtained from individuals that were: normal (n=48); with benign breast disease (n=20); with diagnosed but treated breast cancer (no evidence of disease (NED) (n=45); with active breast cancer (n=57); with treated colon cancer (NED) (n=8); with active colon cancer (N=14); with active lung cancer (N=10); with active ovarian cancer (n=6); and with active prostate cancer (N=13). The mean OA519 values, determined as described in Example 22, are shown in FIGS. 22 and 23 for each of these categories, along with the standard error and range of values.

Figure 22:
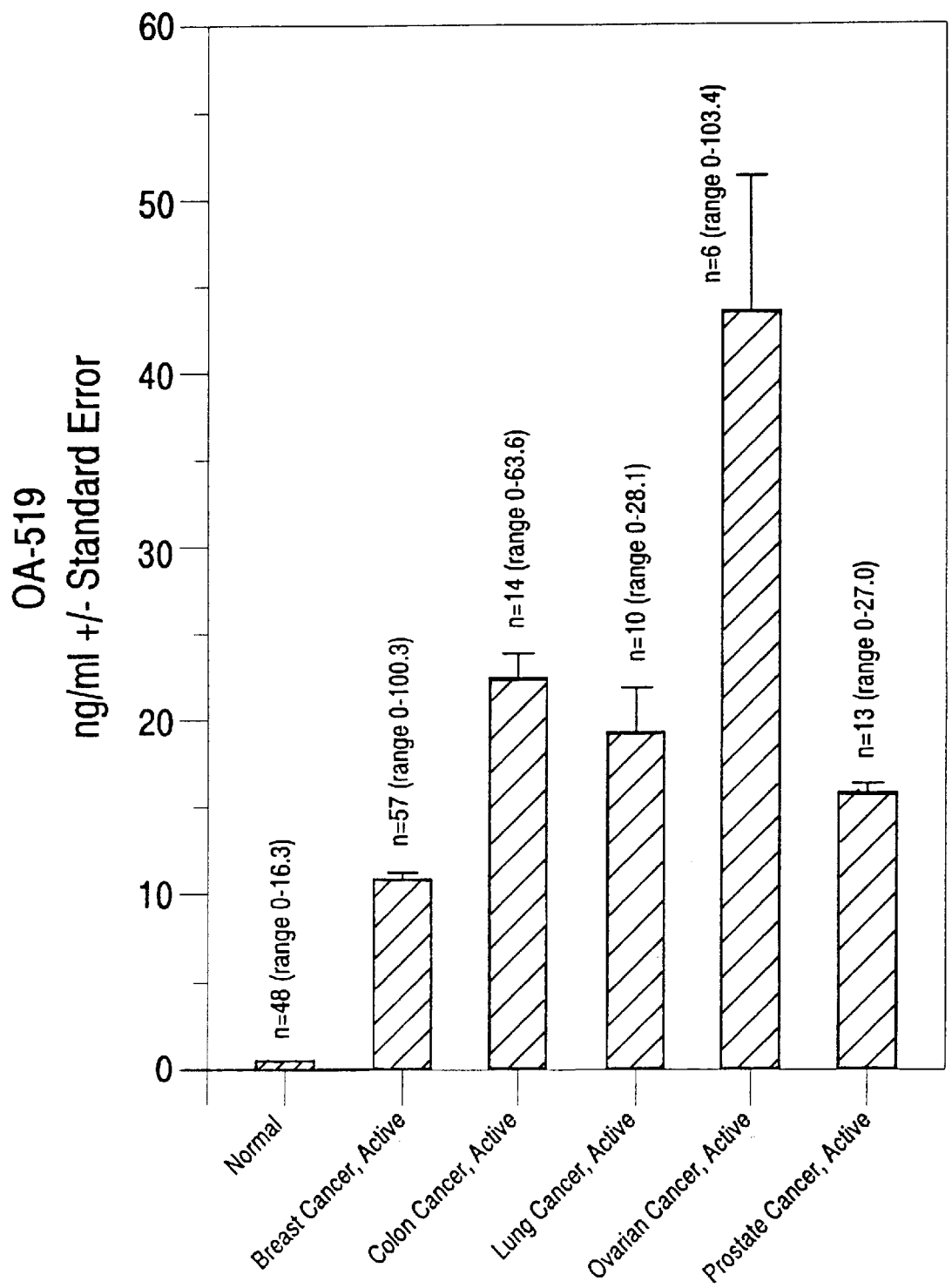
FIG. 22 shows the amount of OA-519 detected in the blood of patients diagnosed with different types of cancer.
Figure 23:
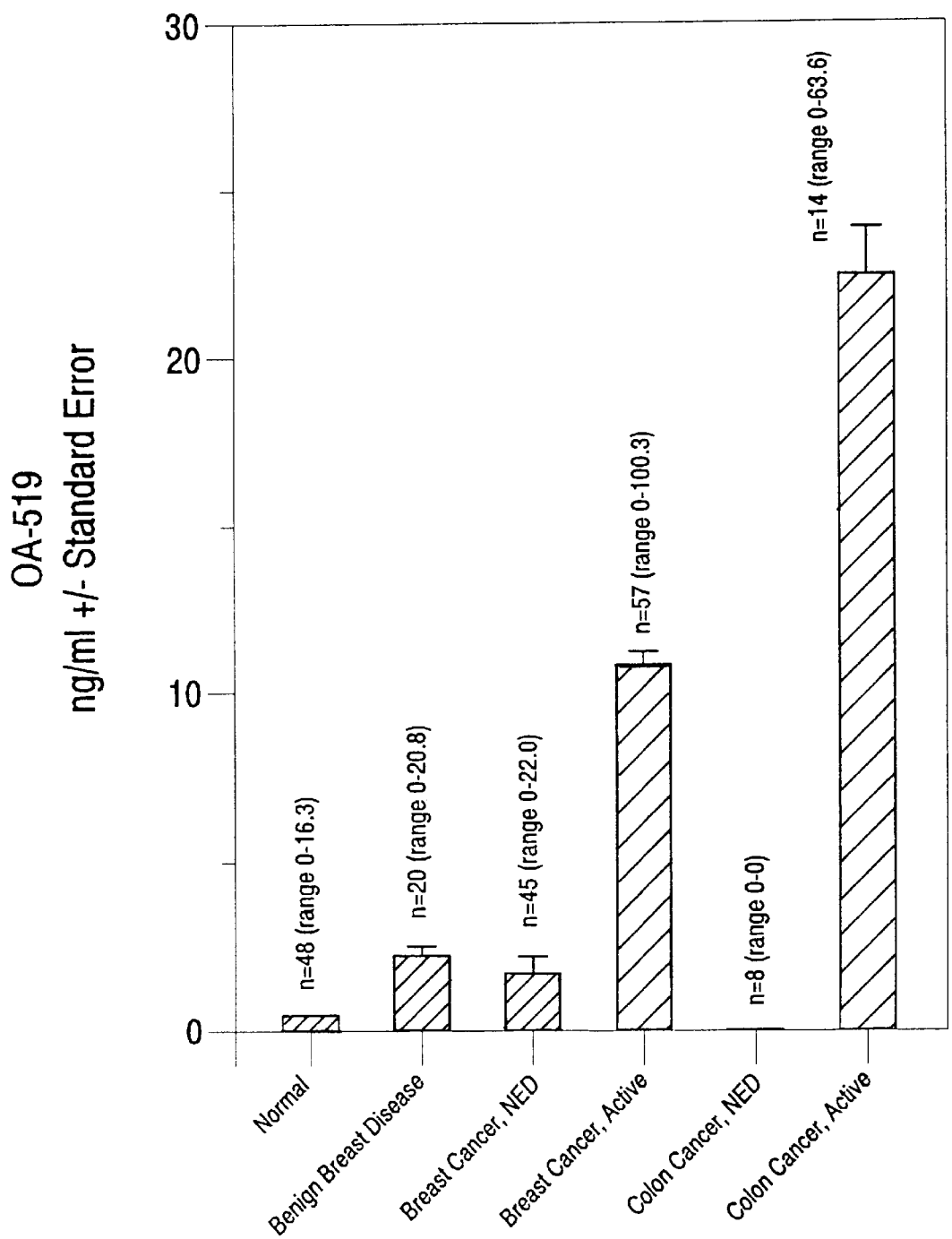
FIG. 23 shows the amount of OA-519 detected in the blood of cancer patients with active or inactive disease.

FIG. 22 summarizes the ELISA results for plasma samples from patients with breast, colon, lung, ovarian or prostate cancer, and compares the mean OA-519 level for these cancer patients to the mean OA-519 level in normal individuals. As shown in FIG. 22, OA-519 is elevated in the plasma of these cancer patients, compared to normal control individuals. In FIG. 23, the plasma level of OA-519 in patients with active cancer is compared to that of in individuals with no evidence of active disease. For both diseases tested (breast cancer and colon cancer) these data clearly shown that these cancer patients contain higher levels of OA519™ in their blood than the normal or benign breast diseased individuals.

Example 24

Figure 24:
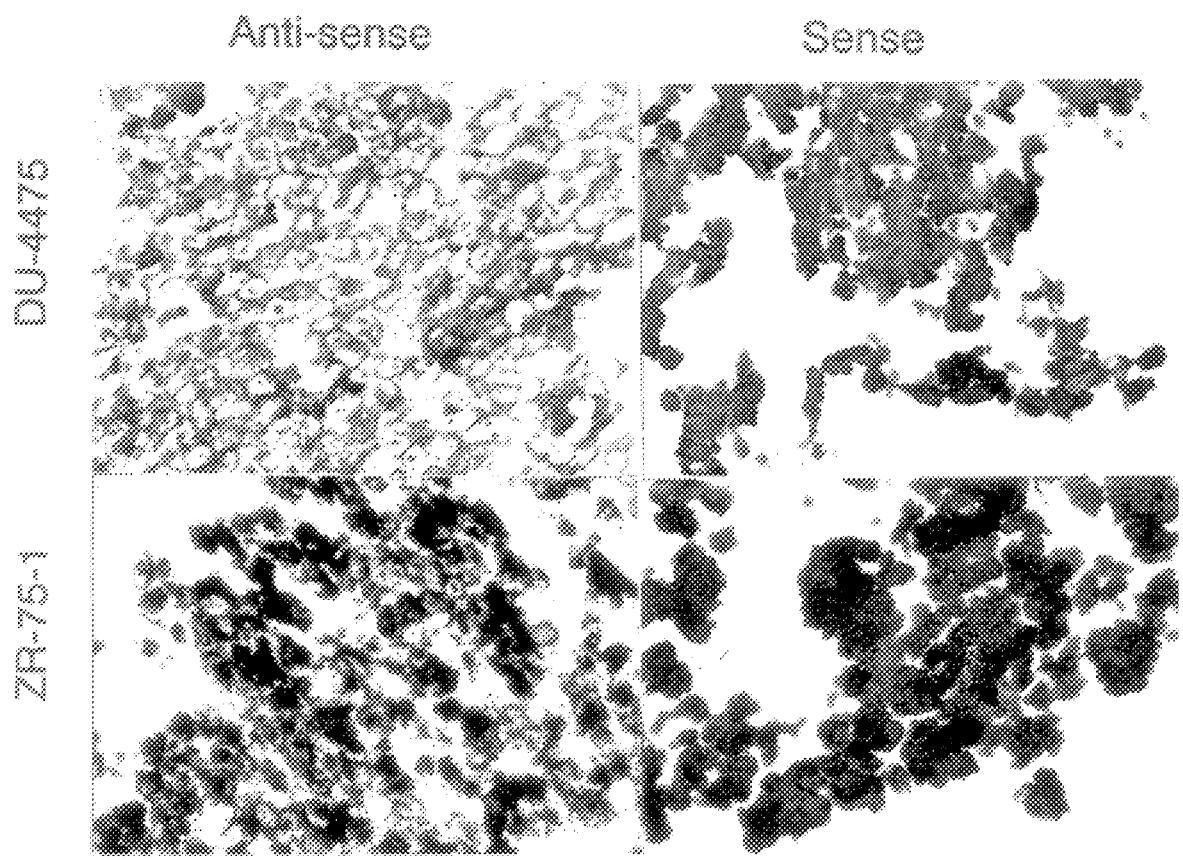
FIG. 24 shows detection of OA-519$_{FAS}$ expression in tumor cell lines by in situ hybridization of riboprobes having FAS sequence.

OA-519 expression analyzed by in situ hybridization cDNA from a ZR-75-1 library yielded a 1.6 kb probe, pFAS 1.6, showing ~85 % nucleotide identity with 3' sequences of rat fatty acid synthase cDNA. On Northern blots of total ZR-75-1 RNA, this probe hybridized with a single ~9.5 kb message (data not shown). In situ hybridization for OA-519 in formalin-fixed paraffin-embedded ZR-75-1 and DU-4475 human breast cells using digoxigenin-labeled riboprobes derived from pFAS 1.6 in Bluescript II is shown in FIG. 24. The left panel is anti-sense, while the right panel is the sense control. Anti-sense riboprobes generated from pFAS 1.6 yielded a substantially stronger hybridization signal with ZR-75-1 cells than with DU-4475 cells (FIG. 24), showing that message levels and protein levels were concordant. Thus, cells that express OA-519 can be detected by either immunohistochemistry or in situ hybridization.

These data together suggest that OA-519 over-expression is from increased message levels, due either to increased transcriptional activation or to prolonged message stability. Increased OA-519 levels were not likely due to prolongation of OA-519 protein half-life since OA-519 protein over-expression was accompanied by OA-519 message over-expression. Similarly, experiments finding equivalent pFAS 1.6 hybridization signals among Southern blots of cell lines differing widely in OA-519 expression indicated that over-expression was not likely from gene amplification.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A polypeptide consisting of the amino acid sequence: leu tyr ser gly asn asp val thr asp ile ser asp asp arg phe pro lys pro pro glu ile ala asn gly tyr val glu lys leu phe arg tyr gln cys (SEQ ID NO: 1).

2. A substantially pure polypeptide consisting essentially of the amino acid sequence: leu tyr ser gly asn asp val thr asp ile ser asp asp arg phe pro lys pro pro glu ile ala asn gly tyr val glu lys leu phe arg tyr gln cys (SEQ ID NO: 1), wherein the polypeptide is specifically immunologically cross-reactive with polyclonal antibodies which specifically bind the gene product of the hpr gene.

3. The substantially pure polypeptide of claim 2, wherein the polypeptide is a protein which is specifically immunologically cross-reactive with polyclonal antiserum elicited by immunization with haptoglobin 1 or haptoglobin 2.

4. A substantially pure protein, said protein having an amino acid sequence containing at least the amino acid sequence: leu tyr ser gly asn asp val thr asp ile ser asp asp arg phe pro lys pro pro glu ile ala asn gly tyr val glu lys leu phe arg tyr gln cys (SEQ ID NO: 1), wherein the protein is specifically immunologically cross-reactive with polyclonal antiserum elicited by immunization with the gene product of the hpr gene.

5. The substantially pure protein of claim 4, wherein the protein is the gene product of the hpr gene.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Homo sapiens ( x i ) SEQUENCE DESCRIPTION: SEQ ID NO:1:

Leu Tyr Ser Gly Asn Asp Val Thr Asp Ile Ser Asp Asp Arg Phe Pro
1               5                   10                  15

Lys Pro Pro Glu Ile Ala Asn Gly Tyr Val Glu Lys Leu Phe Arg Tyr
            20                  25                  30

Gln Cys ( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Homo sapiens ( x i ) SEQUENCE DESCRIPTION: SEQ ID NO:2:

Phe Ala Ala Leu Gln Glu Glu
1               5

( 2 ) INFORMATION FOR SEQ ID NO:3:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
    ( A ) ORGANISM: Homo sapiens ( x i ) SEQUENCE DESCRIPTION: SEQ ID NO:3:

```
His Pro Glu Ser Pro Thr Pro Asn Pro Thr Glu Pro Leu Phe Leu Ala
1               5                   10                  15
Gln Ala Glu
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:4:

```
His Ala Val Val Leu Glu
1               5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:5:

```
Arg Ala Ala Leu Gln Glu
1               5
```

( 2 ) INFORMATION FOR SEQ ID NO:6:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:6:

```
GGGCCTGGAG TCTATCATCA ACATCATCCA CAGCTCCCTG GCTGAGCCTC GAGTGAGT        58
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide

```
        ( v i ) ORIGINAL SOURCE:
                ( A ) ORGANISM: Homo sapiens ( x i ) SEQUENCE DESCRIPTION: SEQ ID NO:7:

Leu  Gln  Gln  His  Asp  Val  Ala  Gln  Glu  Gln  Trp  Xaa  Pro
            1                  5                       10

( 2 ) INFORMATION FOR SEQ ID NO:8:

( i ) SEQUENCE CHARACTERISTICS:
                ( A ) LENGTH: 27 amino acids
                ( B ) TYPE: amino acid
                ( C ) STRANDEDNESS: single
                ( D ) TOPOLOGY: linear ( i i ) MOLECULE TYPE: peptide ( v i ) ORIGINAL SOURCE:
                ( A ) ORGANISM: rat ( x i ) SEQUENCE DESCRIPTION: SEQ ID NO:8:

Thr  Lys  Leu  Gln  Gln  His  Asp  Val  Ala  Gln  Gly  Gln  Trp  Asp  Pro  Ser
            1                  5                       10                      15

Gly  Pro  Ala  Pro  Thr  Asn  Leu  Gly  Ala  Leu  Asp
                          20                       25
```